US012036359B2

(12) United States Patent
Milton-Edwards et al.

(10) Patent No.: US 12,036,359 B2
(45) Date of Patent: Jul. 16, 2024

(54) INHALER SYSTEM

(71) Applicant: Norton (Waterford) Limited, Waterford (IE)

(72) Inventors: Mark Milton-Edwards, Cheshire (GB); Guilherme Safioti, Stigtomta (SE); Lena Granovsky, Petah-Tiqva (IL); Michael Reich, Herzliya (IL)

(73) Assignee: Norton (Waterford) Limited, Waterford (IE)

( * ) Notice: Subject to any disclaimer, the term of this patent is extended or adjusted under 35 U.S.C. 154(b) by 174 days.

(21) Appl. No.: 17/864,582

(22) Filed: Jul. 14, 2022

(65) Prior Publication Data

US 2022/0347404 A1 Nov. 3, 2022

Related U.S. Application Data

(63) Continuation of application No. 16/919,628, filed on Jul. 2, 2020, now Pat. No. 11,419,995, which is a
(Continued)

(30) Foreign Application Priority Data

Apr. 30, 2019 (GB) ..................................... 1906078
Jul. 29, 2019 (GB) ..................................... 1910776
(Continued)

(51) Int. Cl.
*A61M 15/00* (2006.01)
*A61B 5/00* (2006.01)
(Continued)

(52) U.S. Cl.
CPC ......... *A61M 15/009* (2013.01); *A61B 5/0826* (2013.01); *A61B 5/4848* (2013.01);
(Continued)

(58) Field of Classification Search
CPC ... A61B 5/0826; A61B 5/4848; A61B 5/7275; A61M 15/0001; A61M 15/0065; G16H 20/10
See application file for complete search history.

(56) References Cited

U.S. PATENT DOCUMENTS 4,972,842 A 11/1990 Korten et al.
4,984,158 A 1/1991 Hillsman
(Continued)

FOREIGN PATENT DOCUMENTS

EP 0667168 A1 8/1995
EP 1135056 B1 8/2006
(Continued)

OTHER PUBLICATIONS

"Freescale Semiconductor Data Sheet", Data Sheet for the Freescale MPL31152A2 Altimeter, Rev 2.2, Jul. 2012, 44 pages.
(Continued)

*Primary Examiner* — John R Downey
(74) *Attorney, Agent, or Firm* — Flaster Greenberg P.C.

(57) ABSTRACT

Provided is a system (10) for determining a probability of an asthma exacerbation in a subject. The system comprises an inhaler (100) for delivering a rescue medicament to the subject. The inhaler has a use-detection system (12B) configured to determine a rescue inhalation performed by the subject using the first inhaler. A sensor system (12A) is configured to measure a parameter relating to airflow during the rescue inhalation. The system further comprises a processor (14) configured to determine a number of the rescue inhalations during a first time period, and receive the parameter measured for at least some of the rescue inhalations. The processor determines, using a weighted model, the probability of the asthma exacerbation based on the number of rescue inhalations and the parameters. The model is weighted such
(Continued)

that the number of rescue inhalations is more significant in the probability determination than the parameters.

20 Claims, 15 Drawing Sheets

Related U.S. Application Data continuation of application No. PCT/IB2020/054056, filed on Apr. 30, 2020.

(30)  Foreign Application Priority Data

| Dec. 20, 2019 | (GB) | .................................... | 1919070 |
|---|---|---|---|
| Dec. 20, 2019 | (GB) | .................................... | 1919076 |
| Dec. 20, 2019 | (GB) | .................................... | 1919081 |
| Mar. 11, 2020 | (GB) | .................................... | 2003534 |

(51) Int. Cl.
*A61B 5/08* (2006.01)
*A61K 31/138* (2006.01)
*C07K 16/24* (2006.01)
*C07K 16/28* (2006.01)
*C07K 16/42* (2006.01)
*G16H 20/10* (2018.01)
*G16H 20/13* (2018.01)
*G16H 50/30* (2018.01)
*G16H 50/70* (2018.01)
*A61M 11/00* (2006.01)

(52) U.S. Cl.
CPC .......... *A61B 5/7275* (2013.01); *A61K 31/138* (2013.01); *A61M 15/0001* (2014.02); *A61M 15/0025* (2014.02); *A61M 15/003* (2014.02); *A61M 15/008* (2014.02); *A61M 15/0091* (2013.01); *C07K 16/244* (2013.01); *C07K 16/247* (2013.01); *C07K 16/2866* (2013.01); *C07K 16/4291* (2013.01); *G16H 20/10* (2018.01); *G16H 20/13* (2018.01); *G16H 50/30* (2018.01); *G16H 50/70* (2018.01); *A61M 11/00* (2013.01); *A61M 15/0026* (2014.02); *A61M 2202/064* (2013.01); *A61M 2205/05* (2013.01); *A61M 2205/18* (2013.01); *A61M 2205/3327* (2013.01); *A61M 2205/3331* (2013.01); *A61M 2205/3358* (2013.01); *A61M 2205/3584* (2013.01); *A61M 2205/502* (2013.01); *A61M 2205/505* (2013.01); *A61M 2205/52* (2013.01); *A61M 2230/30* (2013.01); *A61M 2230/40* (2013.01); *C07K 2317/21* (2013.01); *C07K 2317/24* (2013.01); *C07K 2317/52* (2013.01)

(56)  References Cited

U.S. PATENT DOCUMENTS

| 5,071,453 | A | 12/1991 | Hradek et al. |
|---|---|---|---|
| 5,363,842 | A | 11/1994 | Mishelevich et al. |
| 5,469,750 | A | 11/1995 | Rubsamen et al. |
| 5,505,192 | A | 4/1996 | Samiotes et al. |
| 5,809,997 | A | 9/1998 | Wolf et al. |
| 5,839,429 | A | 11/1998 | Marnfeldt et al. |
| 5,842,468 | A | 12/1998 | Denyer et al. |
| 5,887,586 | A | 3/1999 | Dahlbaeck et al. |
| 5,957,125 | A | 9/1999 | Sagstetter et al. |
| 6,004,277 | A | 12/1999 | Maharaj et al. |
| 6,283,923 | B1 | 9/2001 | Finkelstein et al. |
| 6,285,731 | B1 | 9/2001 | Marnfeldt et al. |
| 6,390,088 | B1 | 5/2002 | Noehl et al. |
| 6,446,627 | B1 | 9/2002 | Bowman et al. |
| 6,693,546 | B2 | 2/2004 | Skardon |
| 6,752,145 | B1 | 6/2004 | Bonney et al. |
| 6,932,083 | B2 | 8/2005 | Jones et al. |
| 6,958,691 | B1 | 10/2005 | Robertson et al. |
| 6,978,780 | B1 | 12/2005 | Marnfeldt et al. |
| 6,990,975 | B1 | 1/2006 | Jones et al. |
| 7,072,738 | B2 | 7/2006 | Robertson et al. |
| 7,151,456 | B2 | 12/2006 | Godfrey et al. |
| 7,191,777 | B2 | 3/2007 | Brand et al. |
| 7,198,172 | B2 | 4/2007 | Lintell et al. |
| 7,233,228 | B2 | 6/2007 | Lintell et al. |
| 7,249,687 | B2 | 7/2007 | Anderson |
| 7,347,200 | B2 | 3/2008 | Jones et al. |
| 7,383,837 | B2 | 6/2008 | Robertson et al. |
| 7,424,888 | B2 | 9/2008 | Lintell et al. |
| 7,495,546 | B2 | 2/2009 | Lintell |
| 7,587,988 | B2 | 9/2009 | Bowman et al. |
| 7,837,648 | B2 | 11/2010 | Blair et al. |
| 8,231,541 | B2 | 7/2012 | Colquitt et al. |
| 8,231,573 | B2 | 7/2012 | Edwards et al. |
| 8,240,301 | B2 | 8/2012 | Spaargaren et al. |
| 8,342,172 | B2 | 1/2013 | Levy et al. |
| 8,403,865 | B2 | 3/2013 | Halperin et al. |
| 8,424,517 | B2 | 4/2013 | Sutherland et al. |
| 8,464,707 | B2 | 6/2013 | Jongejan et al. |
| 8,491,493 | B2 | 7/2013 | Colquitt et al. |
| 8,547,239 | B2 | 10/2013 | Peatfield et al. |
| 8,620,591 | B2 | 12/2013 | Wegerich |
| 8,758,262 | B2 | 6/2014 | Rhee et al. |
| 8,795,170 | B2 | 8/2014 | Pipke |
| 8,807,131 | B1 | 8/2014 | Chan et al. |
| 8,960,189 | B2 | 2/2015 | Morrison |
| 8,978,966 | B2 | 3/2015 | Walsh et al. |
| 8,997,735 | B2 | 4/2015 | Zierenberg et al. |
| 9,056,174 | B2 | 6/2015 | Bradshaw et al. |
| 9,174,009 | B2 | 11/2015 | Peatfield et al. |
| 9,188,579 | B2 | 11/2015 | Shen et al. |
| 9,237,862 | B2 | 1/2016 | Bussa et al. |
| 9,242,056 | B2 | 1/2016 | Andersen et al. |
| 9,265,445 | B2 | 2/2016 | Shinar et al. |
| 9,339,616 | B2 | 5/2016 | Denny et al. |
| 9,364,619 | B2 | 6/2016 | Polidoro et al. |
| 9,427,534 | B2 | 8/2016 | Bruin et al. |
| 9,463,291 | B2 | 10/2016 | Imran |
| 9,468,729 | B2 | 10/2016 | Sutherland et al. |
| 9,550,031 | B2 | 1/2017 | Van Sickle et al. |
| 9,555,201 | B2 | 1/2017 | Collins et al. |
| 9,694,147 | B2 | 7/2017 | Peatfield et al. |
| 9,736,642 | B2 | 8/2017 | Ostrander et al. |
| 9,782,551 | B2 | 10/2017 | Morrison et al. |
| 9,839,398 | B2 | 12/2017 | Yamamori et al. |
| 9,911,308 | B2 | 3/2018 | Edwards et al. |
| 9,956,360 | B2 | 5/2018 | Germinario et al. |
| 9,962,507 | B2 | 5/2018 | Germinario et al. |
| 9,962,508 | B2 | 5/2018 | Bruin et al. |
| 10,016,134 | B2 | 7/2018 | Hansen et al. |
| 10,019,555 | B2 | 7/2018 | Manice et al. |
| 10,046,121 | B2 | 8/2018 | Kolb et al. |
| 10,255,412 | B2 | 4/2019 | Hogg et al. |
| 10,363,384 | B2 | 7/2019 | Dyche et al. |
| 10,406,305 | B2 | 9/2019 | Collins et al. |
| 10,531,838 | B2 | 1/2020 | Barretto et al. |
| 10,556,070 | B2 | 2/2020 | Van Sickle et al. |
| 10,664,572 | B2 | 5/2020 | Bitran et al. |
| 10,726,954 | B2 | 7/2020 | Su et al. |
| 10,810,283 | B2 | 10/2020 | Shetty et al. |
| 10,849,314 | B2 | 12/2020 | Genzow et al. |
| 2002/0185128 | A1 | 12/2002 | Theobald et al. |
| 2003/0192535 | A1 | 10/2003 | Christrup et al. |
| 2003/0205229 | A1 | 11/2003 | Crockford et al. |
| 2004/0089299 | A1 | 5/2004 | Bonney et al. |
| 2004/0117062 | A1 | 6/2004 | Bonney et al. |
| 2005/0043674 | A1 | 2/2005 | Blair et al. |
| 2005/0119604 | A1 | 6/2005 | Bonney et al. |
| 2005/0161467 | A1 | 7/2005 | Jones et al. |
| 2005/0172958 | A1 | 8/2005 | Singer et al. |
| 2005/0247312 | A1 | 11/2005 | Davies et al. |
| 2005/0251289 | A1 | 11/2005 | Bonney et al. |

(56) References Cited

U.S. PATENT DOCUMENTS

| | | |
|---|---|---|
| 2006/0254581 A1 | 11/2006 | Genova et al. |
| 2007/0017506 A1 | 1/2007 | Bell et al. |
| 2007/0251950 A1 | 11/2007 | Bacon |
| 2007/0295329 A1 | 12/2007 | Lieberman et al. |
| 2008/0178872 A1 | 7/2008 | Genova et al. |
| 2008/0230057 A1 | 9/2008 | Sutherland et al. |
| 2009/0151718 A1 | 6/2009 | Hunter et al. |
| 2009/0194104 A1 | 8/2009 | Van et al. |
| 2009/0221308 A1 | 9/2009 | Erner et al. |
| 2010/0036266 A1 | 2/2010 | Nysaether et al. |
| 2010/0094099 A1 | 4/2010 | Levy et al. |
| 2010/0242960 A1 | 9/2010 | Zangerle et al. |
| 2010/0250280 A1 | 9/2010 | Sutherland et al. |
| 2011/0041845 A1 | 2/2011 | Solomon et al. |
| 2011/0226242 A1 | 9/2011 | Von et al. |
| 2011/0282693 A1 | 11/2011 | Craft |
| 2011/0283997 A1 | 11/2011 | Walsh et al. |
| 2013/0008436 A1 | 1/2013 | Von Hollen et al. |
| 2013/0053719 A1 | 2/2013 | Wekell |
| 2013/0151162 A1 | 6/2013 | Harris et al. |
| 2013/0239957 A1 | 9/2013 | Pinfold |
| 2013/0269685 A1 | 10/2013 | Jung et al. |
| 2013/0298905 A1 | 11/2013 | Levin et al. |
| 2014/0106324 A1 | 4/2014 | Adams et al. |
| 2014/0182584 A1 | 7/2014 | Sutherland et al. |
| 2014/0264653 A1 | 9/2014 | Cheng et al. |
| 2014/0305429 A1 | 10/2014 | Lewis |
| 2015/0150484 A1 | 6/2015 | Wekell |
| 2015/0283341 A1 | 10/2015 | Adams et al. |
| 2016/0082208 A1 | 3/2016 | Ballam et al. |
| 2016/0089089 A1 | 3/2016 | Kakkar et al. |
| 2016/0128389 A1 | 5/2016 | Lamb et al. |
| 2016/0129182 A1 | 5/2016 | Schuster et al. |
| 2016/0144141 A1 | 5/2016 | Sabharwal et al. |
| 2016/0166766 A1 | 6/2016 | Schuster et al. |
| 2016/0228657 A1 | 8/2016 | Sutherland |
| 2016/0256639 A1 | 9/2016 | Van Sickle et al. |
| 2016/0283686 A1 | 9/2016 | Hu et al. |
| 2016/0314256 A1 | 10/2016 | Su et al. |
| 2017/0079557 A1 | 3/2017 | Lauk |
| 2017/0109493 A1 | 4/2017 | Hogg et al. |
| 2017/0140125 A1 | 5/2017 | Hogg et al. |
| 2017/0161461 A1 | 6/2017 | Delangre et al. |
| 2017/0164892 A1 | 6/2017 | Sezan et al. |
| 2017/0173279 A1 | 6/2017 | Sutherland et al. |
| 2017/0213145 A1 | 7/2017 | Pathak et al. |
| 2017/0246406 A1 | 8/2017 | Sutherland |
| 2017/0258993 A1 | 9/2017 | Pizzochero et al. |
| 2017/0262613 A1 | 9/2017 | Ljungberg |
| 2017/0325734 A1 | 11/2017 | Sutherland et al. |
| 2017/0363673 A1 | 12/2017 | Mukherjee |
| 2018/0011988 A1 | 1/2018 | Ziegler et al. |
| 2018/0052964 A1 | 2/2018 | Adelson |
| 2018/0056018 A1 | 3/2018 | Canvin et al. |
| 2018/0085540 A1 | 3/2018 | Dantsker et al. |
| 2018/0125365 A1 | 5/2018 | Hunter et al. |
| 2018/0161530 A1 | 6/2018 | Ganton et al. |
| 2018/0221600 A1 | 8/2018 | Shears et al. |
| 2019/0014824 A1 | 1/2019 | Yazbeck et al. |
| 2019/0030262 A1 | 1/2019 | Ziegler et al. |
| 2019/0083001 A1 | 3/2019 | Stamatopoulos et al. |
| 2019/0102522 A1 | 4/2019 | Barrett et al. |
| 2019/0108912 A1 | 4/2019 | Spurlock et al. |
| 2019/0111222 A1 | 4/2019 | Wang et al. |
| 2019/0134330 A1 | 5/2019 | Germinario et al. |
| 2019/0167209 A1 | 6/2019 | Annoni et al. |
| 2019/0189258 A1 | 6/2019 | Barrett et al. |
| 2019/0272925 A1 | 9/2019 | Barrett et al. |
| 2019/0290129 A1 | 9/2019 | Hanina et al. |
| 2019/0307648 A1 | 10/2019 | Bartos |
| 2019/0313919 A1 | 10/2019 | Pritchard et al. |
| 2019/0328278 A1 | 10/2019 | Zabel et al. |
| 2019/0385727 A1 | 12/2019 | Manice et al. |
| 2020/0003437 A1 | 1/2020 | Breen |
| 2020/0058403 A1 | 2/2020 | Barrett et al. |
| 2020/0098459 A1 | 3/2020 | Hanina et al. |
| 2020/0135334 A1 | 4/2020 | Rajasekhar et al. |
| 2020/0143939 A1 | 5/2020 | Semen et al. |
| 2020/0188613 A1 | 6/2020 | Van Sickle et al. |
| 2020/0193806 A1 | 6/2020 | Finke et al. |
| 2020/0250554 A1 | 8/2020 | Shao et al. |
| 2021/0068706 A1 | 3/2021 | De Backer |

FOREIGN PATENT DOCUMENTS

| | | |
|---|---|---|
| EP | 1992381 A1 | 11/2008 |
| EP | 3228345 A1 | 10/2017 |
| EP | 2414978 B1 | 12/2018 |
| JP | H04500915 A | 2/1992 |
| JP | H11511676 A | 10/1999 |
| JP | 2002543935 A | 12/2002 |
| JP | 2013516265 A | 5/2013 |
| WO | 8911823 A1 | 12/1989 |
| WO | 9522365 A1 | 8/1995 |
| WO | 9638084 A1 | 12/1996 |
| WO | 9963901 A1 | 12/1999 |
| WO | 9964095 A2 | 12/1999 |
| WO | 0069496 A1 | 11/2000 |
| WO | 03063754 A1 | 8/2003 |
| WO | 2005020023 A2 | 3/2005 |
| WO | 2008149959 A1 | 12/2008 |
| WO | 2009003989 A1 | 1/2009 |
| WO | 2011010282 A1 | 1/2011 |
| WO | 2011083377 A1 | 7/2011 |
| WO | 2011157561 A1 | 12/2011 |
| WO | 2013085910 A1 | 6/2013 |
| WO | 2013098714 A1 | 7/2013 |
| WO | 2013532019 A | 8/2013 |
| WO | 2013182951 A1 | 12/2013 |
| WO | 2016043601 A1 | 3/2016 |
| WO | 2016090260 A1 | 6/2016 |
| WO | 2017005605 A1 | 1/2017 |
| WO | 2017051389 A1 | 3/2017 |
| WO | 2017129521 A1 | 8/2017 |
| WO | 2017141194 A1 | 8/2017 |
| WO | 2017176693 A1 | 10/2017 |
| WO | 2017176704 A1 | 10/2017 |
| WO | 2017180980 A1 | 10/2017 |
| WO | 2017189712 A1 | 11/2017 |
| WO | 2017192778 A1 | 11/2017 |
| WO | 2018128976 A1 | 7/2018 |
| WO | 2018134552 A1 | 7/2018 |
| WO | 2018134553 A1 | 7/2018 |
| WO | 2018160073 A1 | 9/2018 |
| WO | 2019022620 A1 | 1/2019 |
| WO | 2019226576 A1 | 11/2019 |

OTHER PUBLICATIONS

Colthorpe, Paul, et al., "Adding Electronics to the Breezhaler: Satisfying the Needs of Patients and Regulators", Respiratory Drug Delivery, 2018, pp. 71-80.

Friedman, Jerome, et al., "Additive Logistic Regression: A Statistical View of Boosting", The Annals of Statistics, 2000, vol. 28, No. 2, Stanford University, Stanford, California, 2000, pp. 337-407.

Friedman, J.H., "Stochastic Gradient Boosting", Computational Statistics & Data Analysis 2002, 38(4), (https://doi.org/10.1016/S0167-9473(01)00065-2), 2002, pp. 367-378.

Gamble, Jacqueline, et al., "The Prevalence of Non-adherence in Difficult Asthma", American Journal of Respiratory and Critical Care Medicine, vol. 180, 2009, Belfast, Northern Ireland, 2009, pp. 817-822.

Liu, Andrew, et al., "Advances in Asthma 2015: Across the Lifespan", Journal of Allergy and Clinical Immunology, Elsevier, Amsterdam, NL, vol. 138, No. 2., Aug. 3, 2016, pp. 397-404.

Meltzer, E.O., et al., "Use of the Asthma Control Questionnaire to predict future risk of asthma exacerbation", Journal of Allergy and Clinical Immunology, Elsevier Amsterdam, NL, vol. 127, No. 1, Dec. 31, 2011, pp. 167-172.

Reddel, et al., "An Official American Thoracic Society/European Respiratory Society Statement: Asthma Control and Exacerba-

(56) References Cited

OTHER PUBLICATIONS tions", American journal of respiratory and critical care medicine, vol. 180, 2009-01-01 00:00:00.0, pp. 59-99.

Safioti, Guilherme, et al., "A Predictive Model for Clinical Asthma Exacerbations Using Albuterol eMDPI (ProAir Digihaler): A Twelve-Week, Open Label Study", ATS Annual Conference, Dallas, TX, May 22, 2019, p. 693.

Sulaiman, Imran, et al., "A randomised clinical trial of feedback on inhaler adherence and technique in patients with severe uncontrolled asthma", Eur Respir J 2018; 51: 1701126 [https://doi.org/10.1183/13993003.01126-2017], 20018, 9 pages.

Finkelstein, Joseph, and In Cheol Jeong. "Machine learning approaches to personalize early prediction of asthma exacerbations." Annals of the New York Academy of Sciences vol. 1387, 1 (2017): 153-165. doi:10.1111/nyas. 13218.

Taylor TE, Lacalle Muls H, Costello RW, Reilly RB. Estimation of inhalation flow profile using audio-based methods to assess inhaler medication adherence. Kou YR, ed. PLoS One. 2018.

INHALER SYSTEM

CROSS-REFERENCE TO RELATED APPLICATIONS

This application is a continuation of U.S. Non-Provisional application Ser. No. 16/919,628, filed Jul. 2, 2020, which is a continuation of PCT Patent Application No. PCT/IB2020/054056, filed Apr. 30, 2020, which claims the benefit of Great Britain Provisional Patent Application No. 1906078.9, filed Apr. 30, 2019, Great Britain Provisional Patent Application No. 1910776.2, filed Jul. 29, 2019, Great Britain Provisional Patent Application No. 1919070.1, filed Dec. 20, 2019, Great Britain Provisional Patent Application No. 1919081.8, filed Dec. 20, 2019, Great Britain Provisional Patent Application No. 1919076.8, filed Dec. 20, 2019, and Great Britain Provisional Patent Application No. 2003534.1, filed Mar. 11, 2020, the disclosures of which are incorporated herein by reference in their entireties.

FIELD OF THE INVENTION

This disclosure relates to an inhaler system, and particularly systems and methods for determining a probability of a respiratory disease exacerbation.

BACKGROUND OF THE INVENTION

Many respiratory diseases, such as asthma or chronic obstructive pulmonary disease (COPD), are life-long conditions where treatment involves the long-term administration of medicaments to manage the patients' symptoms and to decrease the risks of irreversible changes. There is currently no cure for diseases like asthma and COPD. Treatment takes two forms. First, a maintenance aspect of the treatment is intended to reduce airway inflammation and, consequently, control symptoms in the future. The maintenance therapy is typically provided by inhaled corticosteroids, alone or in combination with long-acting bronchodilators and/or muscarinic antagonists. Secondly, there is also a rescue (or reliever) aspect of the therapy, where patients are given rapid-acting bronchodilators to relieve acute episodes of wheezing, coughing, chest tightness and shortness of breath. Patients suffering from a respiratory disease, such as asthma or COPD may also experience episodic flare-ups, or exacerbations, in their respiratory disease, where symptoms rapidly worsen. In the worst case, exacerbations may be life-threatening.

The ability to identify an impending respiratory disease exacerbation would improve action plans and provide opportunities for pre-emptive treatment, before the patient's condition requires, for example, unscheduled visits to or from a medical practitioner, hospital admission and administering of systemic steroids.

There is therefore a need in the art for improved methods of identifying the risk of an impending respiratory disease exacerbation.

SUMMARY OF THE INVENTION

Accordingly, the present disclosure provides a system for determining a probability of an asthma exacerbation in a subject, the system comprising:
a first inhaler for delivering a rescue medicament to the subject, the first inhaler having a use-detection system configured to determine a rescue inhalation performed by the subject using the first inhaler; an optional second inhaler for delivering a maintenance medicament to the subject during a routine inhalation,
wherein the system comprises a sensor system configured to measure a parameter relating to airflow during said rescue inhalation and/or during said routine inhalation using the second inhaler when included in the system; and
a processor configured to:
determine a number of said rescue inhalations during a first time period;
receive said parameter measured for at least some of said rescue and/or routine inhalations; and determine, using a weighted model, said probability of the asthma exacerbation based on said number of rescue inhalations and said parameters, wherein the model is weighted such that the number of rescue inhalations is more significant in said probability determination than said parameters.

Use of both the number of rescue inhalations and the parameter relating to airflow during the rescue and/or routine inhalations leads to a more accurate predictive model for predicting the asthma exacerbation than, for example, a model which neglects either one of these factors. Moreover, it has been found that, in the case of asthma exacerbations, the number of rescue inhalations is more significant in the probability determination than the parameter. Accordingly, enhancement of the accuracy of the probability determination stems from weighting the model such that the number of rescue inhalations is more significant in the probability determination than the parameter. This contrasts with the trend for predicting a COPD exacerbation, for which the inhalation parameter was found to be more significant in the exacerbation prediction than the number of rescue inhalations.

BRIEF DESCRIPTION OF THE DRAWINGS

The present invention will now be described in more detail with reference to the accompanying drawings, which are not intended to be limiting.

DETAILED DESCRIPTION OF THE INVENTION

Figure 1:
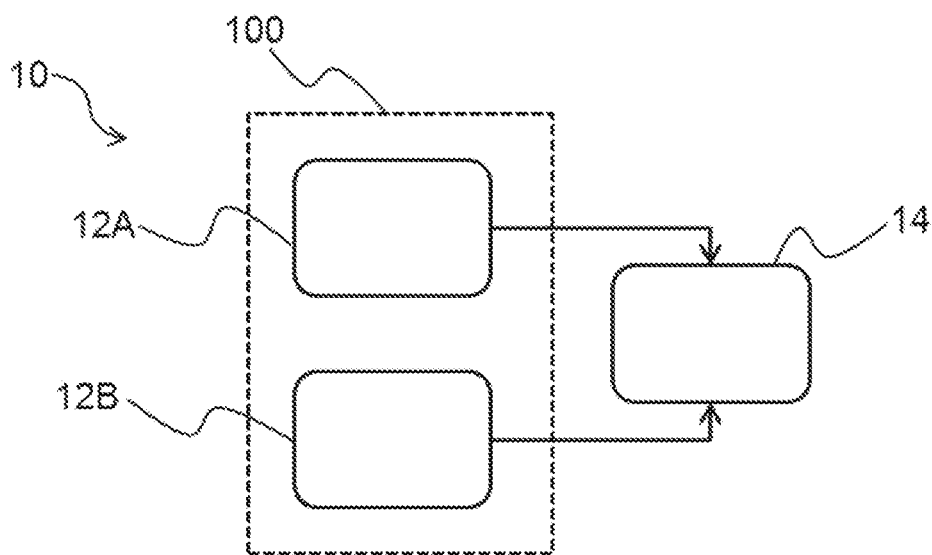
FIG. 1 shows a block diagram of a system according to an embodiment.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the figures to indicate the same or similar parts.

Asthma and COPD are chronic inflammatory disease of the airways. They are both characterized by variable and recurring symptoms of airflow obstruction and bronchospasm. The symptoms include episodes of wheezing, coughing, chest tightness and shortness of breath.

The symptoms are managed by avoiding triggers and by the use of medicaments, particularly inhaled medicaments. The medicaments include inhaled corticosteroids (ICSs) and bronchodilators.

Inhaled corticosteroids (ICSs) are steroid hormones used in the long-term control of respiratory disorders. They function by reducing the airway inflammation. Examples include budesonide, beclomethasone (dipropionate), fluticasone (propionate), mometasone (furoate), ciclesonide and dexamethasone (sodium). Parentheses indicate preferred salt or ester forms.

Different classes of bronchodilators target different receptors in the airways. Two commonly used classes are $β_2$-agonists and anticholinergics.

β2-Adrenergic agonists (or "$β_2$-agonists") act upon the $β_2$-adrenoceptors which induces smooth muscle relaxation, resulting in dilation of the bronchial passages. Examples of long-acting $β_2$-agonists (LABAs) include formoterol (fumarate), salmeterol (xinafoate), indacaterol (maleate), bambuterol (hydrochloride), clenbuterol (hydrochloride), olodaterol (hydrochloride), carmoterol (hydrochloride), tulobuterol (hydrochloride) and vilanterol (triphenylacetate). An example of a short-acting β2-agonist (SABA) is albuterol (sulfate).

Typically short-acting bronchodilators provide a rapid relief from acute bronchoconstriction (and are often called "rescue" or "reliever" medicines), whereas long-acting bronchodilators help control and prevent longer-term symptoms. However, some rapid-onset long-acting bronchodilators may be used as rescue medicines, such as formoterol (fumarate). Thus, a rescue medicine provides relief from acute bronchoconstriction. The rescue medicine is taken as-needed/prn (pro re nata). The rescue medicine may also be in the form of a combination product, e.g. ICS-formoterol (fumarate), typically budesonide-formoterol (fumarate). Thus, the rescue medicine is preferably a SABA or a rapid-acting LABA, more preferably albuterol (sulfate) or formoterol (fumarate), and most preferably albuterol (sulfate).

Albuterol (also known as salbutamol), typically administered as the sulfate salt, is a preferred rescue medicine of the present disclosure.

Anticholinergics (or "antimuscarinics") block the neurotransmitter acetylcholine by selectively blocking its receptor in nerve cells. On topical application, anticholinergics act predominantly on the $M_3$ muscarinic receptors located in the airways to produce smooth muscle relaxation, thus producing a bronchodilatory effect. Examples of long-acting muscarinic antagonists (LAMAs) include tiotropium (bromide), oxitropium (bromide), aclidinium (bromide), ipratropium (bromide) glycopyrronium (bromide), oxybutynin (hydrochloride or hydrobromide), tolterodine (tartrate), trospium (chloride), solifenacin (succinate), fesoterodine (fumarate) and darifenacin (hydrobromide).

A number of approaches have been taken in preparing and formulating these medicaments for delivery by inhalation, such as via a dry powder inhaler (DPI), a pressurized metered dose inhaler (pMDI) or a nebulizer.

According to the GINA (Global Initiative for Asthma) Guidelines, a step-wise approach is taken to the treatment of asthma. At step 1, which represents a mild form of asthma, the patient is given an as needed SABA, such as albuterol sulfate. The patient may also be given an as-needed low-dose ICS-formoterol, or a low-dose ICS whenever the SABA is taken. At step 2, a regular low-dose ICS is given alongside the SABA, or an as-needed low-dose ICS-formoterol. At step 3, a LABA is added. At step 4, the doses are increased and at step 5, further add-on treatments are included such as an anticholinergic or a low-dose oral corticosteroid. Thus, the respective steps may be regarded as treatment regimens, which regimens are each configured according to the degree of acute severity of the respiratory disease.

COPD is a leading cause of death worldwide. It is a heterogeneous long-term disease comprising chronic bronchitis, emphysema and also involving the small airways. The pathological changes occurring in patients with COPD are predominantly localised to the airways, lung parenchyma and pulmonary vasculature. Phenotypically, these changes reduce the healthy ability of the lungs to absorb and expel gases.

Bronchitis is characterised by long-term inflammation of the bronchi. Common symptoms may include wheezing, shortness of breath, cough and expectoration of sputum, all of which are highly uncomfortable and detrimental to the patient's quality of life. Emphysema is also related to long-term bronchial inflammation, wherein the inflammatory response results in a breakdown of lung tissue and progressive narrowing of the airways. In time, the lung tissue loses its natural elasticity and becomes enlarged. As such, the efficacy with which gases are exchanged is reduced and respired air is often trapped within the lung. This results in localised hypoxia, and reduces the volume of oxygen being delivered into the patient's bloodstream, per inhalation. Patients therefore experience shortness of breath and instances of breathing difficulty.

Patients living with COPD experience a variety, if not all, of these symptoms on a daily basis. Their severity will be determined by a range of factors but most commonly will be correlated to the progression of the disease. These symptoms, independent of their severity, are indicative of stable COPD and this disease state is maintained and managed through the administration of a variety drugs. The treatments are variable, but often include inhaled bronchodilators, anticholinergic agents, long-acting and short-acting $\beta_2$-agonists and corticosteroids. The medicaments are often administered as a single therapy or as combination treatments.

Patients are categorised by the severity of their COPD using categories defined in the GOLD Guidelines (Global Initiative for Chronic Obstructive Lung Disease, Inc.). The categories are labelled A-D and the recommended first choice of treatment varies by category. Patient group A are recommended a short-acting muscarinic antagonist (SAMA) prn or a short-acting $\beta_2$-aginist (SABA) prn. Patient group B are recommended a long-acting muscarinic antagonist (LAMA) or a long-acting $\beta_2$-aginist (LABA). Patient group C are recommended an inhaled corticosteroid (ICS)+a LABA, or a LAMA. Patient group D are recommended an ICS+a LABA and/or a LAMA.

Patients suffering from respiratory diseases like asthma or COPD suffer from periodic exacerbations beyond the baseline day-to-day variations in their condition. An exacerbation is an acute worsening of respiratory symptoms that require additional therapy, i.e. a therapy going beyond their maintenance therapy.

For asthma, the additional therapy for a moderate exacerbation are repeated doses of SABA, oral corticosteroids and/or controlled flow oxygen (the latter of which requires hospitalization). A severe exacerbation adds an anticholinergic (typically ipratropium bromide), nebulized SABA or IV magnesium sulfate.

For COPD, the additional therapy for a moderate exacerbation are repeated doses of SABA, oral corticosteroids and/or antibiotics. A severe exacerbation adds controlled flow oxygen and/or respiratory support (both of which require hospitalization).

An exacerbation within the meaning of the present disclosure includes both moderate and severe exacerbations.

The present disclosure is directed to a treatment approach which predicts exacerbations of a respiratory disease to allow an early intervention in the patient's treatment, thereby improving the outcome for the patient.

Provided is a system for determining a probability (or likelihood) of an asthma exacerbation in a subject.

The system comprises a first inhaler for delivering a rescue medicament to the subject. The rescue medicament may be suitable for treating a worsening of respiratory symptoms, for example by effecting rapid dilation of the bronchi and bronchioles upon inhalation of the medicament. The first inhaler has a use-detection system configured to determine a rescue inhalation performed by the subject using the first inhaler. The system optionally includes a second inhaler for delivering a maintenance medicament to the subject during a routine inhalation. A sensor system is configured to measure a parameter relating to airflow during the rescue inhalation and/or during the routine inhalation, when the second inhaler is included in the system.

The rescue medicament is as defined hereinabove and is typically a SABA or a rapid-onset LABA, such as formoterol (fumarate). The rescue medicine may also be in the form of a combination product, e.g. ICS-formoterol (fumarate), typically budesonide-formoterol (fumarate). Such an approach is termed "MART" (maintenance and rescue therapy). However, the presence of a rescue medicine indicates that it is a first inhaler within the meaning of the present disclosure since the presence of the rescue medicament is determinative in the weighted model used. It therefore covers both a rescue medicament and a combination rescue and maintenance medicament. In contrast, the second inhaler, when present, is only used for the maintenance aspect of the therapy and not for rescue purposes. The key difference is that the first inhaler may be used as-needed, whereas the second inhaler is intended for use at regular, pre-defined times.

The system further comprises a processor configured to determine a number of the rescue inhalations during a first time period, and receive the parameter measured for at least some of the rescue and/or routine inhalations. The processor then determines, using a weighted model, the probability of the asthma exacerbation based on the number of rescue inhalations and the parameters. The model is weighted such that the number of rescue inhalations is more significant in the probability determination than the parameters. Further provided is a method for determining the probability of an asthma exacerbation in a subject, which method employs the weighted model. Any preferred embodiments discussed in respect of the system may be applied to the methods, and vice versa.

Attempts have been made to assess the risk of an impending respiratory disease exacerbation, such as an asthma or COPD exacerbation, by monitoring various subject-related and environmental factors. Challenges have been encountered concerning which factors should be taken into account, and which neglected. Neglecting factors which only have a minimal or negligible influence on the risk determination may enable determination of the risk more efficiently, for example using less computational resources, such as processing resources, battery power, memory requirements, etc. Of greater importance is the requirement to improve the accuracy with which an impending respiratory disease exacerbation may be determined. A more accurate risk determination may facilitate a more effective warning system so that the appropriate clinical intervention may be delivered to the subject. Thus, more accurate assessment of the risk of exacerbation may have the potential to guide intervention for a subject at acute risk.

For a higher probability of exacerbation, a step change in the treatment regimen may, for instance, be justified to a regimen configured for subjects at greater acute risk. Alternatively, in the case of a lower probability of exacerbation over a prolonged period, enhanced accuracy of the probability determination may be used as guidance to justify downgrading or even removal of an existing treatment regimen. This may, for example, mean that the subject may no longer be required to take a higher dose of medicament which is no longer commensurate with the status of their respiratory disease.

The present inventors have found, from carrying out extensive clinical studies, which will be explained in more detail herein below, that enhanced accuracy in determining the probability of an asthma disease exacerbation is achieved by employing a weighted model which bases the asthma exacerbation probability calculation both on the number of rescue inhalations of a rescue medicament performed by the subject during a (first) time period and a parameter relating to airflow during inhalations of a rescue and/or maintenance medicament.

The first time period corresponds to the sample period over which the number of rescue inhalations is counted. The first time period may be, for example, 1 to 15 days. This sample period may be selected such that the period allows for an indicative number of rescue inhalations to occur. A sample period which is too short may not permit sufficient inhalation data to be collected for reliable exacerbation prediction, whilst a sample period which is too long may have an averaging effect which renders shorter term trends which are of diagnostic or predictive significance less distinguishable.

Use of both the number of rescue inhalations and the parameter may lead to a more accurate predictive model than, for example, a model which neglects either one of these factors. Moreover, it has been found from the clinical studies that the number of rescue inhalations, including trends relating to rescue inhaler usage, is more significant in the probability determination for asthma than the parameter relating to airflow during the inhalations. The parameter may still be a significant factor in determining the probability of an asthma exacerbation, but may exert less overall influence on the probability than the number of rescue inhalations. Accordingly, further enhancement of the accuracy of the probability determination stems from weighting the model such that the number of rescue inhalations is more significant in the probability determination than the parameter.

The model may have, for example, a first weighting coefficient associated with the number of rescue inhalations and a second weighting coefficient associated with the parameters. When standardized to account for the different units used to quantify the number of rescue inhalations (or related trends of rescue medicament use) and the parameters, the first weighting coefficient may be larger than the second weighting coefficient, thereby ensuring that the number of rescue inhalations is more significant in the asthma probability determination than the parameter.

The probability determination is partly based on the number of rescue inhalations. Basing the determination on the number of rescue inhalations may mean that the model uses the absolute number of rescue inhalations during the first time period and/or one or more trends based on the number of rescue inhalations. Such trends are not the number of rescue inhalations per se, but are variations in the number of rescue inhalations.

The trends based on the number of rescue inhalations may, for example, include the number of inhalations performed during a particular period in the day. The number of night-time inhalations may therefore, for instance, be included as a factor in the number of inhalations. The processor may, for example, be equipped with suitable clock functionality in order to record such time of day rescue medicament use.

The first weighting coefficient may weight the absolute number of rescue inhalations and/or the one or more trends based on the number of rescue inhalations.

More generally, the number of rescue inhalations (e.g. including any related trends) may have a significance/importance (e.g. weight) in the model (relative to the other factors) of 40% to 95%, preferably 55% to 95%, more preferably 60% to 85%, and most preferably 60% to 80%, e.g. about 60% or about 80%.

The probability determination is also based on the parameter relating to airflow during the rescue inhalation and/or during the routine inhalation using the second inhaler when present. The parameter may correspond to a single factor relating to airflow during inhalation or may include a plurality of such factors. For example, the parameter may be at least one of a peak inhalation flow, an inhalation volume, an inhalation duration, and an inhalation speed. The time to peak inhalation flow may, for example, provide a measure of the inhalation speed.

Basing the determination on the parameters may mean that the model uses the one or more factors relating to airflow during the inhalations and/or one or more trends associated with the respective factor or factors. Such trends correspond to variations in the respective factor(s).

The second weighting coefficient may weight the one or more factors relating to airflow during the inhalations and/or the one or more trends associated with the respective factor or factors.

More generally, the inhalation parameters (e.g. including any related trends) may have a significance/importance (e.g. weight) in the model of 2% to 49% or 2% to 30%, preferably 2% to 45%, more preferably 5% to 40%, and most preferably 10% to 35%, e.g. about 10% or about 35%.

The probability of the asthma exacerbation may be the probability of the impending asthma exacerbation occurring within an exacerbation period subsequent to the first time period. The model may thus enable determination of the probability of the asthma exacerbation occurring during a predetermined period, termed the "exacerbation period", which follows the first period during which the inhalation data, i.e. the number of rescue inhalations and the parameter data, are collected. The exacerbation period may be, for example, 1 to 10 days, such as 5 days. The exacerbation period may be selected based on the capability of the model to predict an exacerbation within such a period, whilst also ensuring that the predetermined period is sufficiently long for appropriate therapeutic steps to be taken, if necessary.

In some embodiments, a biometric parameter may be included in the weighted model to further improve its accuracy. In such embodiments, the processor may, for example, be configured to receive the biometric parameter. A data input unit may, for instance, be included in the system to enable the subject and/or healthcare provider to input the biometric parameter.

The model may, for example, be weighted such that the biometric parameter has a lower significance than the number of rescue inhalations in the probability determination. In other words, a third weighting coefficient may be associated with the biometric parameter (or biometric parameters), which third weighting coefficient may be smaller than the first weighting coefficient associated with the number of rescue inhalations. The third weighting coefficient may be larger or smaller than the second weighting coefficient associated with the parameter relating to airflow.

Preferably, the third weighting coefficient is smaller than the second weighting coefficient. In order of predictive power, the rescue medicament use may thus have the greatest influence, then the inhalation parameter, and then the biometric parameter.

The biometric parameter may be, for instance, one or more selected from body weight, height, body mass index, blood pressure, including systolic and/or diastolic blood pressure, sex, race, age, smoking history, sleep/activity patterns, exacerbation history, other treatments or medicaments administered to the subject, etc. In an embodiment, the biometric parameter includes age, body mass index and exacerbation history. In a preferred embodiment, the biometric parameter includes exacerbations and medical history, body mass index, and blood pressure, for example systolic and/or diastolic blood pressure.

More generally, the biometric parameter may have a significance/importance (e.g. weight) in the model of 1% to 15%, preferably 1% to 12%, more preferably 3% to 10%, and most preferably 4% to 10%, e.g. about 5% or about 8%.

In a non-limiting example, the number of rescue inhalations (e.g. including any related trends) has a significance/importance (e.g. weight) in the model (relative to the other factors) of 40% to 95%, preferably 55% to 90%, more preferably 60% to 85%, and most preferably 60% to 80%, e.g. about 60% or about 80%; the inhalation parameters (e.g. including any related trends) has a significance/importance (e.g. weight) in the model of 2% to 49%, preferably 2% to 45%, more preferably 5% to 40%, and most preferably 10% to 35%, e.g. about 10% or about 35%; and the biometric parameter has a significance/importance (e.g. weight) in the model of 1% to 15%, preferably 1% to 12%, more preferably 3% to 10%, and most preferably 4% to 10%, e.g. about 5% or about 8%.

More generally, additional data sources may also be added to the model, such as environmental data relating to the weather or pollution levels. Such additional data may be weighted such as to have less significance on the probability determination than the number of rescue inhalations and optionally less significance than the inhalation parameter data.

The number of maintenance/routine inhalations may alternatively or additionally represent useful information for predicting an exacerbation, since fewer maintenance/routine inhalations (indicative of poorer compliance with a maintenance medication regimen) may result in an increased risk of an exacerbation.

In a relatively simple example, an increase in the number of rescue inhalations using the first inhaler (relative to a baseline period for the subject in question) and/or a decrease in the number of routine inhalations using the second inhaler (indicative of lower adherence to a treatment regimen), may together with inhalation parameters indicating worsening lung function leading to a higher probability of the respiratory disease exacerbation.

Figure 17:
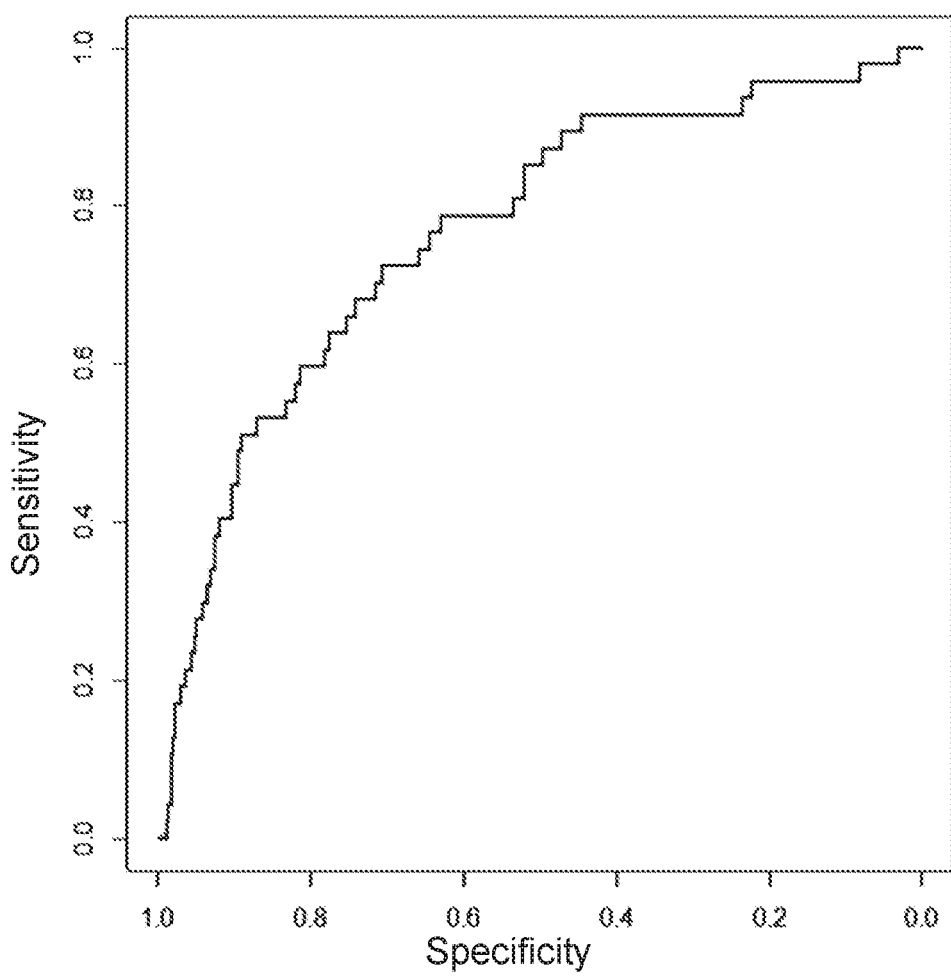
FIG. 17 shows a receiver operating characteristic (ROC) curve analysis of a model for determining the probability of an impending COPD exacerbation.
Figure 18:
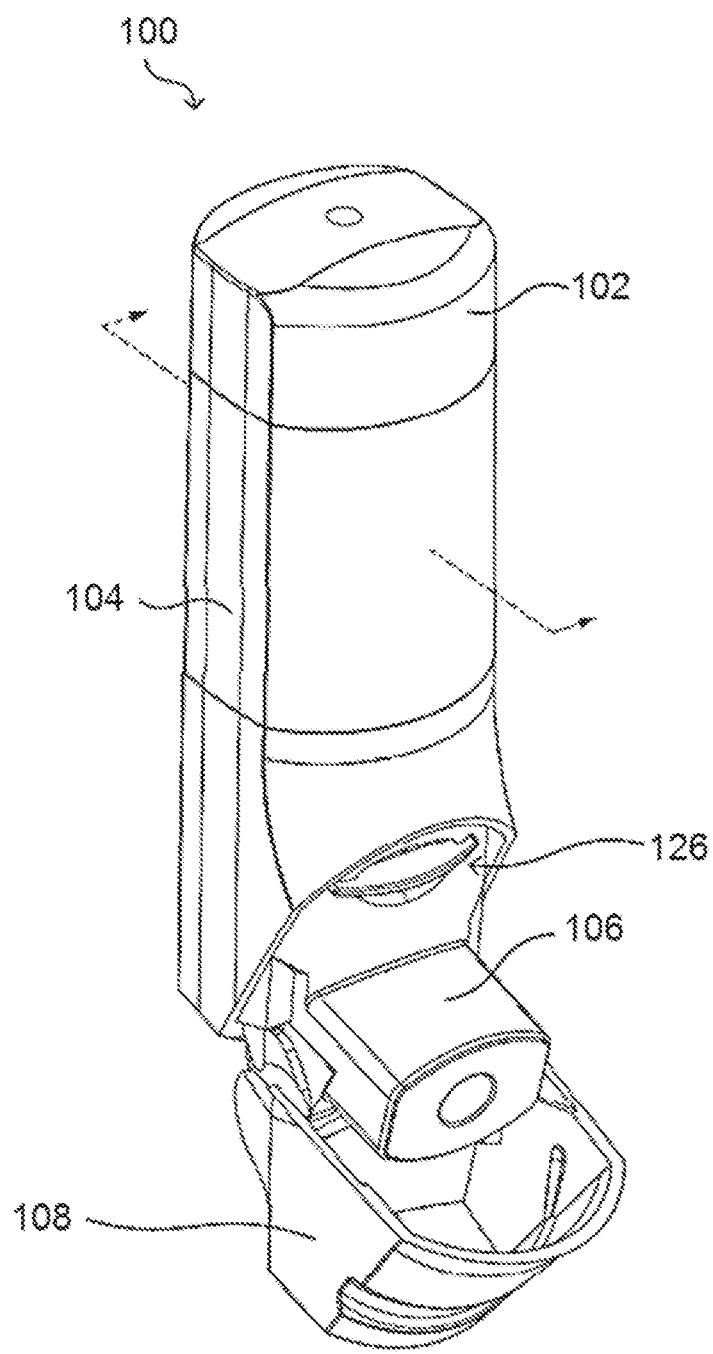
FIG. 18 shows a front perspective view of an inhaler.

In a specific example, a decrease in adherence to a maintenance medicament regimen from 80% to 55%, an increase in rescue inhaler use by 67.5%, a drop in peak inhalation flow by 34%, a drop in inhalation volume by 23% (all changes from patient's baseline), two exacerbations in the previous year, and a BMI over 28 may result in a probability of an asthma exacerbation in the next 5 days, with an ROC-AUC (see the below discussion of FIGS. 8 and 17) of 0.87.

More generally, the number of rescue inhalations (e.g. including any related trends in the number of rescue inhalations) may be the most significant factor in the probability determination.

The model may be a linear model or may be a non-linear model. The model may be, for instance, a machine learning model. A supervised model, such as a supervised machine learning model, may, for example, be used. Irrespective of the specific type of model employed, the model is constructed to be more sensitive, i.e. responsive, to the number of inhalations than the inhalation parameters, as previously described. It is this sensitivity which may correspond to the "weighting" of the weighted model.

In a non-limiting example, the model is constructed using a decision trees technique. Other suitable techniques, such as building a neural network or a deep learning model may also be contemplated by the skilled person.

Irrespective of the respiratory disease exacerbation being predicted, the processor of the system may determine the probability of the exacerbation based on the number of inhalations, the inhalation parameters and the indication of a status of the respiratory disease being experienced by the subject. The inclusion of the indication in the prediction may enhance the accuracy of the prediction. This is because the user-inputted indication may assist to validate or enhance the predictive value of the probability assessment relative to that derived from, for example, consideration of the number of inhalations and the inhalation parameters without such a user-inputted indication.

In an embodiment, the processor determines an initial probability of the respiratory disease exacerbation based on the recorded inhalation or inhalations, and the received inhalation parameter or parameters, but not on the indication. The initial probability may, for example, be calculated using a weighted model, e.g. as described above. The probability, i.e. the overall probability, may then be determined based on the inhalation(s), the parameter(s) and the received indication of the status of the respiratory disease being experienced by the subject. For example, the overall probability may be determined based on the initial probability and the received indication.

The initial probability may, for example, determine the risk of an exacerbation during the subsequent 10 days. The overall probability, taking the indication of the status of the respiratory disease being experienced by the subject, may, for example, determine the risk of an exacerbation during the subsequent 5 days. Thus, the inclusion of the indication in the probability determination may enable a more accurate shorter term prediction.

By including the user-inputted indication in the probability determination, one or more of: positive and negative predictive values, the sensitivity of the prediction, i.e. the capability of the system/method to correctly identify those at risk (true positive rate), and the specificity of the prediction, i.e. the capability of the system/method to correctly identify those not at risk (true negative rate), may be enhanced.

The inhalations and inhalation parameter data may indicate, for example, a deviation from the subject's baseline as early as 10 days prior to an exacerbation. By including the user-inputted indication in the subsequent prediction, the positive and negative predictive values, and the sensitivity and specificity of the predictive system/method, may be improved.

The processor may, for example, be configured to control a user interface to issue a prompt to the user so that the user inputs the indication. The prompt may be issued based on the initial probability determined from the inhalation(s) and the inhalation parameter(s), but not on the indication. For example, the prompt may be issued based on the initial probability reaching or exceeding a predetermined threshold. In this manner, the user may be prompted by the system to input the indication on the basis of the initial probability signaling a potential impending exacerbation. By the user then inputting the indication, the (overall) probability which also takes account of the indication may assist to confirm or validate the initial probability.

This may be, for instance, regarded as an "analytics data driven" use of the indication: the user input is requested when the inhalation and inhalation parameter data indicate possible worsening of the subject's respiratory disease.

The user interface may, for example, prompt the user or subject to provide the indication via a pop-up notification link to complete a short questionnaire. The logic determining when this pop-up notification is provided may, for example, be driven by shifts in key variables, such as changes in the number and/or time of rescue and/or controller inhalations, and inhalation parameters.

Alternatively or additionally, the system may be configured to receive the indication when the user opts to input the indication via the user interface. For example, when the healthcare provider decides that the indication may usefully enhance the initial probability determination. This may, for instance, be regarded as an "on request" use of the indication: the request being made by the patient or his/her physician, e.g. prior to or during an assessment by the healthcare professional.

In this manner, the user may only be prompted to input the indication when this is deemed necessary by the system and/or healthcare provider. This may advantageously reduce burden on the subject, and render it more likely that the subject will input the indication when asked or prompted to do so, i.e. when such input would be desirable in relation to monitoring the subject's respiratory disease. Inputting the indication in these embodiments may thus be more likely than the scenario in which the subject is routinely prompted to input the indication.

In an embodiment, the user interface is configured to provide a plurality of user-selectable respiratory disease status options. In this case, the indication is defined by user-selection of at least one of the status options.

For example, the user interface may display a questionnaire comprising questions whose answers correspond to the indication. The user, e.g. the subject or his/her health care provider, may input the answers to the questions using the user interface.

The questionnaire may be relatively short, i.e. with relatively few questions, in order to minimize burden on the subject. The number and nature of the questions may nevertheless be such as to ensure that the indication enables the exacerbation probability determination to be enhanced relative to the scenario where no indication is inputted.

More generally, the object of the questionnaire is to ascertain a contemporaneous or relatively recent (e.g. within the past 24 hours) indication in order to obtain "in the moment" understanding of the subject's well-being (in respect of their respiratory disease) with a few timely questions which are relatively quickly answered. The questionnaire may be translated into the local language of the subject.

Conventional control questionnaires, and especially the most established being ACQ/T (Asthma Control Questionnaire/Test) in asthma, or CAT (COPD Assessment Test) in COPD tend to focus on patient recall of symptoms in the past. Recall bias, and a focus on the past instead of the present is likely to negatively influence their value for the purposes of predictive analysis.

The following is provided by way of non-limiting example of such a questionnaire. The subject may select from the following status options for each question: All of the time (5); Most of the time (4); Some of the time (3); A little (2); None (1).

1. How 'often are you experiencing', or 'Rate your' shortness of breath?
2. How 'often are you experiencing', or 'Rate your' coughing?
3. How 'often are you experiencing', or 'Rate your' wheezing?
4. How 'often are you experiencing', or 'Rate your' chest tightness?
5. How 'often are you experiencing', or 'Rate your' night symptoms/affecting sleep?
6. How 'often are you experiencing', or 'Rate your' limitation at work, school or home?

An alternative example questionnaire is also provided:
1. Are you having more respiratory symptoms than usual (Y/N)? If yes:
2. More chest tightness or shortness of breath (Y/N)?
3. More cough (Y/N)?
4. More wheezing (Y/N)?
5. Is it affecting your sleep (Y/N)?
6. Is it limiting your activities at home/work/school (Y/N)?

The answers to the questions may, for example, be used to calculate a score, which score is included in, or corresponds to, the indication of the status of the respiratory disease being experienced by the subject.

In an embodiment, the user interface is configured to provide the status options in the form of selectable icons, e.g. emoji-type icons, checkboxes, a slider, and/or a dial. In this way, the user interface may provide a straightforward and intuitive way of inputting the indication of the status of the respiratory disease being experienced by the subject. Such intuitive inputting may be particularly advantageous when the subject himself/herself is inputting the indication, since the relatively facile user-input may be minimally hampered by any worsening of the subject's respiratory disease.

Any suitable user interface may be employed for the purpose of enabling user-input of the indication of the status of the respiratory disease being experienced by the subject. For example, the user interface may comprise or consist of a (first) user interface of a user device. The user device may be, for example, a personal computer, a tablet computer, and/or a smart phone. When the user device is a smart phone, the (first) user interface may, for instance, correspond to the touchscreen of the smart phone.

In an embodiment, the processor of the system may be at least partly included a (first) processor included in the user device. Alternatively or additionally, the first inhaler and/or the second inhaler may, for example, include a (second) processor, and the processor of the system may be at least partly included in the (second) processor included in the inhaler.

A method is provided for determining a probability of an asthma exacerbation in a subject, the method comprising: determining a number of rescue inhalations of a rescue medicament performed by the subject during a first time period, the medicament being suitable for treating the subject's acute respiratory disease; measuring a parameter relating to airflow during at least some of the rescue inhalations and/or during routine inhalations performed by the subject of a maintenance medicament; and determining, using a weighted model, the probability of the asthma exacerbation based on the number of rescue inhalations and the parameters, wherein the model is weighted such that the number of rescue inhalations is more significant in the probability determination than the parameters.

Further provided is a method for treating an asthma exacerbation in a subject, the method comprising: performing the method as defined above; determining whether the probability reaches or exceeds a predetermined upper threshold; or determining whether the probability reaches or is lower than a predetermined lower threshold; and treating the asthma based on the probability reaching or exceeding the predetermined upper threshold; or based on the probability reaching or being lower than the predetermined lower threshold.

The treating may comprise using an inhaler to deliver the rescue medicament to the subject when the probability reaches or exceeds the predetermined upper threshold.

The treatment may comprise modifying an existing treatment. The existing treatment may comprise a first treatment regimen, and the modifying the existing treatment of the asthma may comprise changing from the first treatment regimen to a second treatment regimen based on the probability reaching or exceeding the predetermined upper threshold, wherein the second treatment regimen is configured for higher risk of asthma exacerbation than the first treatment regimen.

The more accurate risk determination using the weighted model may facilitate a more effective warning system so that the appropriate clinical intervention may be delivered to the subject. Thus, more accurate assessment of the risk of exacerbation may have the potential to guide intervention for a subject at acute risk. In particular, the intervention may include implementing the second treatment regimen. This may, for example, involve progressing the subject to a higher step specified in the GINA or GOLD guidelines. Such preemptive intervention may mean that the subject need not proceed to suffer the exacerbation, and be subjected to the associated risks, in order for the progression to the second treatment regimen to be justified.

In an embodiment, the second treatment regimen comprises administering a biologics medication to the subject. The relatively high cost of biologics means that stepping up the subject's treatment to include administering of a biologics medication tends to require careful consideration and justification. The systems and methods according to the present disclosure may provide a reliable metric, in terms of the risk of the subject experiencing an exacerbation, to justify administering of a biologics medication. For example, should the determined probability reach or surpass an upper threshold indicative of a high risk of exacerbation on a predetermined minimum number of occasions, the administering of the biologics medication may be quantitatively justified, and the biologics medication may be administered accordingly.

More generally, the biologics medication may comprise one or more of omalizumab, mepolizumab, reslizumab, benralizumab, and dupilumab.

Modifying the existing treatment of the asthma may comprise changing from the first treatment regimen to a third treatment regimen based on the probability reaching or being lower than the predetermined lower threshold, wherein the third treatment regimen is configured for lower risk of asthma exacerbation than the first treatment regimen.

In the case, for instance, of a lower probability of exacerbation over a relatively prolonged period, enhanced accuracy of the probability determination may be used as guidance to justify downgrading or even removal of an existing treatment regimen. In particular, the subject may be moved from the first treatment regimen onto the third treatment regimen which is configured for lower risk of respiratory disease exacerbation than the first treatment regimen. This may, for example, involve progressing the subject to a lower step specified in the GINA or GOLD guidelines.

A method is provided for diagnosing an asthma exacerbation, the method comprising: performing the method for determining a probability of an asthma exacerbation in a subject as defined above; determining whether the probability reaches or exceeds a predetermined upper threshold indicative of the asthma exacerbation; and diagnosing the asthma exacerbation based on the probability reaching or exceeding the predetermined upper threshold.

A method is also provided for diagnosing an acute severity of asthma in a subject, the method comprising: performing the method for determining a probability of an asthma exacerbation in a subject as defined above; determining whether the probability reaches or exceeds a predetermined upper threshold indicative of the respiratory disease being more severe; or determining whether the probability reaches or is lower than a predetermined lower threshold indicative of the asthma being less severe; and diagnosing a higher severity based on the probability reaching or exceeding the predetermined upper threshold; or diagnosing a lower severity based on the probability reaching or being lower than the predetermined lower threshold.

Further provided is a method for demarcating a subpopulation of subjects, the method comprising: performing the method defined above for each subject of a population of subjects, thereby determining the probability of the asthma exacerbation for each subject of said population; providing a threshold probability or range of the probabilities which distinguishes the probabilities determined for the subpopulation from the probabilities determined for the rest of the population; and demarcating the subpopulation from the rest of the population using the threshold probability or range of the probabilities.

FIG. 1 shows a block diagram of a system 10 according to an embodiment. The system 10 comprises a first inhaler 100 and a processor 14. The first inhaler 100 may be used to deliver a rescue medicament, such as a SABA, to the subject. The SABA may include, for example, albuterol. The first inhaler 100 may include a sensor system 12A and/or a use-detection system 12B.

The system 10 may, for example, be alternatively termed "an inhaler assembly".

The first inhaler may, for example, be alternatively termed "a rescue inhaler".

The second inhaler may, for example, be alternatively termed "a maintenance inhaler" or "a controller inhaler".

The number of rescue inhalations is determined by a use-detection system 12B included in the first inhaler 100.

A sensor system 12A may be configured to measure the parameter. The sensor system 12A may, for example, comprise one or more sensors, such as one or more pressure sensors, temperature sensors, humidity sensors, orientation sensors, acoustic sensors, and/or optical sensors. The pressure sensor(s) may include a barometric pressure sensor (e.g. an atmospheric pressure sensor), a differential pressure sensor, an absolute pressure sensor, and/or the like. The sensors may employ microelectromechanical systems (MEMS) and/or nanoelectromechanical systems (NEMS) technology.

A pressure sensor(s) may be particularly suitable for measuring the parameter, since the airflow during inhalation by the subject may be monitored by measuring the associated pressure changes. As will be explained in greater detail with reference to FIGS. 18-22, a pressure sensor may be, for instance, located within or placed in fluid communication with a flow pathway through which air and the medicament is drawn by the subject during inhalation. Alternative ways of measuring the parameter, such as via a suitable flow sensor, will also be apparent to the skilled person.

Alternatively or additionally, the sensor system 12A may comprise a differential pressure sensor. The differential pressure sensor may, for instance, comprise a dual port type sensor for measuring a pressure difference across a section of the air passage through which the subject inhales. A single port gauge type sensor may alternatively be used. The latter operates by measuring the difference in pressure in the air passage during inhalation and when there is no flow. The difference in the readings corresponds to the pressure drop associated with inhalation.

Whilst not shown in FIG. 1, the system 10 may further comprise a second inhaler for delivering a maintenance medicament to the subject during a routine inhalation. The second inhaler may include a sensor system 12A and/or a use-detection system 12B that is distinct from the sensor system 12A and/or the use-detection system 12B of the first inhaler 100. The sensor system 12A of the second inhaler may be configured to measure the parameter during the routine inhalation. For example, the sensor system 12A may include a further pressure sensor, such as a further microelectromechanical system pressure sensor or a further nanoelectromechanical system pressure sensor, in order to measure the parameter during maintenance medicament inhalation.

In this manner, inhalation of either or both the rescue and the maintenance medicaments may be used to gather information relating to the subject's lung function and/or lung health. When both the first and second inhalers are used, the accuracy with which an impending exacerbation can be predicted may be improved by the additional inhalation data supplied by monitoring both routine and rescue medicament inhalations.

Each inhalation may be associated with a decrease in the pressure in the airflow channel relative to when no inhalation is taking place. The point at which the pressure is at its lowest may correspond to the peak inhalation flow. The sensor system 12A may detect this point in the inhalation. The peak inhalation flow may vary from inhalation to inhalation, and may depend on the clinical condition of the subject. Lower peak inhalation flows may, for example, be recorded when the subject is approaching an exacerbation. The term "minimum peak inhalation flow" as used herein may mean the lowest peak inhalation flow recorded for inhalations performed using the first and/or second inhaler during a (second) time period.

The pressure change associated with each inhalation may alternatively or additionally be used to determine an inhalation volume. This may be achieved by, for example, using the pressure change during the inhalation measured by the sensor system 12A to first determine the flow rate over the time of the inhalation, from which the total inhaled volume may be derived. Lower inhalation volumes may be recorded when, for instance, the subject is approaching an exacerbation, since the subject's capacity to inhale may be diminished. The term "minimum inhalation volume" as used herein may mean the lowest inhalation volume recorded for inhalations performed using the first and/or second inhaler during a (third) time period.

The pressure change associated with each inhalation may alternatively or additionally be used to determine an inhalation duration. The time may be recorded, for example, from the first decrease in pressure measured by the pressure sensor 12A, coinciding with the start of the inhalation, to the pressure returning to a pressure corresponding to no inhalation taking place. Lower inhalation durations may be recorded when, for instance, the subject is approaching an exacerbation, since the subject's capacity for inhaling for longer may be diminished. The term "minimum inhalation duration" as used herein may mean the shortest inhalation duration recorded for inhalations performed using the first and/or second inhaler during a (fourth) time period.

In an embodiment, the parameter includes the time to peak inhalation flow, e.g. as an alternative or in addition to the peak inhalation flow, the inhalation volume and/or the inhalation duration. This time to peak inhalation flow parameter may be recorded, for example, from the first decrease in pressure measured by the sensor system 12A, coinciding with the start of the inhalation, to the pressure reaching a minimum value corresponding to peak flow. A subject who is at greater risk of an exacerbation may take a longer time to achieve peak inhalation flow.

In a non-limiting example, the first and/or second inhalers may be configured such that, for a normal inhalation, the respective medicament is dispensed during approximately 0.5 s following the start of the inhalation. A subject's inhalation only reaching peak inhalation flow after the 0.5 s has elapsed, such as after approximately 1.5 s, may be partially indicative of an impending exacerbation.

The use-detection system 12B is configured to register inhalation(s) by the subject (e.g. each rescue inhalation by the subject when the inhaler is a rescue inhaler, or each maintenance inhalation by the subject when the inhaler is a maintenance inhaler). In a non-limiting example, the first inhaler 100 may comprise a medicament reservoir (not shown in FIG. 1), and a dose metering assembly (not shown in FIG. 1) configured to meter a dose of the rescue medicament from the reservoir. The use-detection system 12B may be configured to register the metering of the dose by the dose metering assembly, each metering being thereby indicative of the rescue inhalation performed by the subject using the first inhaler 100. Accordingly, the inhaler 100 may be configured to monitor the number of rescue inhalations of the medicament, since the dose must be metered via the dose metering assembly before being inhaled by the subject. One non-limiting example of the metering arrangement will be explained in greater detail with reference to FIGS. 18-22.

Alternatively or additionally, the use-detection system 12B may register each inhalation in different manners and/or based on additional or alternative feedback that are apparent to the skilled person. For example, the use-detection system 12B may be configured to register an inhalation by the subject when the feedback from the sensor system 12A indicates that an inhalation by the user has occurred (e.g. when a pressure measurement or flow rate exceeds a predefined threshold associated with a successful inhalation). Further, in some examples, the use-detection system 12B may be configured to register an inhalation when a switch of the inhaler or a user input of an external device (e.g. touchscreen of a smartphone) is manually actuated by the subject prior to, during or after inhalation.

A sensor (e.g. a pressure sensor) may, for example, be included in the use-detection system 12B in order to register each inhalation. In such an example, the use-detection system 12B and the sensor system 12A may employ respective sensors (e.g. pressure sensors), or a common sensor (e.g. a common pressure sensor) which is configured to fulfil both use-detecting and inhalation parameter sensing functions.

When a sensor is included in the use-detection system 12B, the sensor may, for instance, be used to confirm that, or assess the degree to which, a dose metered via the dose metering assembly is inhaled by the user, as will be described in greater detail with reference to FIGS. 18-22.

In an embodiment, the sensor system 12A and/or the use-detection system 12B includes an acoustic sensor. The acoustic sensor in this embodiment is configured to sense a noise generated when the subject inhales through the respective inhaler. The acoustic sensor may include, for example, a microphone.

In a non-limiting example, the respective inhaler may comprise a capsule which is arranged to spin when the subject inhales though the device; the spinning of the capsule generating the noise for detection by the acoustic sensor. The spinning of the capsule may thus provide a suitably interpretable noise, e.g. rattle, for deriving use and/or inhalation parameter data.

An algorithm may, for example, be used to interpret the acoustic data in order to determine use data (when the acoustic sensor is included in the use-detection system 12B) and/or the parameter relating to airflow during the inhalation (when the acoustic sensor is included in the sensor system 12A).

For instance, an algorithm as described by Colthorpe et al. in "Adding Electronics to the Breezhaler: Satisfying the Needs of Patients" (Respiratory Drug Delivery 2018; page 71-79) may be used. Once the generated sound is detected, the algorithm may process the raw acoustic data to generate the use and/or inhalation parameter data.

The processor 14 included in the system 10 determines the number of rescue and/or routine inhalations during the first time period and receives the parameter measured for each of the rescue and/or routine inhalations. As schematically shown in FIG. 1 by the arrows between the sensor system 12A and the processor 14, and between the use-detection system 12B and the processor 14, the processor 14 may receive the inhalation and parameter data from the use-detection system 12B and the sensor system 12A respectively. The processor 14 is further configured to determine, using the weighted model, the probability of the respiratory disease exacerbation based on the number of rescue inhalations and the parameters, as will be discussed in greater detail with reference to FIGS. 3-17.

In a non-limiting example, the processor 14 may be provided separately from the respective first and/or second inhaler(s), in which case the processor 14 receives the number of rescue inhalations and parameter data transmitted to it from the sensor system 12A and the use-detection system 12B of the first and/or second inhalers. By processing the data in such an external processing unit, such as in the processing unit of an external device, the battery life of the inhaler may be advantageously preserved.

In an alternative non-limiting example, the processor 14 may be an integral part of the first and/or second inhaler, for example contained within a main housing or top cap (not shown in FIG. 1) of the first and/or second inhaler. In such an example, connectivity to an external device need not be relied upon, since the respiratory disease exacerbation probability determination may be performed exclusively within the first and/or second inhaler. The first and/or second inhaler may, for instance, include a suitable user interface, such as a light or lights, screen, loudspeaker, etc., for communicating the result of the probability determination to the subject. Rather than communicating the probability as a number, more intuitive means of communicating the risk to the subject may in some examples be used, such as using a light of different colors depending on the determined probability. The first and/or second inhaler may thus, for example, prompt the subject to take preemptive steps, such as inhaling the rescue medicament one or more times, to mitigate or remove the risk of an exacerbation.

It may also be contemplated that some of the functions of the processor 14 may be performed by an internal processing unit included in the first and/or second inhaler and other functions of the processor, such as the probability determination itself, may be performed by the external processing unit.

More generally, the system 10 may include, for example, a communication module (not shown in FIG. 1) configured to communicate the determined probability to the subject and/or a healthcare provider, such as a clinician. The subject and/or the clinician may then take appropriate steps based on the determined probability of the respiratory disease exacerbation. When, for instance, a smart phone processing unit is included in the processor, the communication functions of the smart phone, such as SMS, email, Bluetooth®, etc., may be employed to communicate the determined probability to the healthcare provider.

Figure 2:
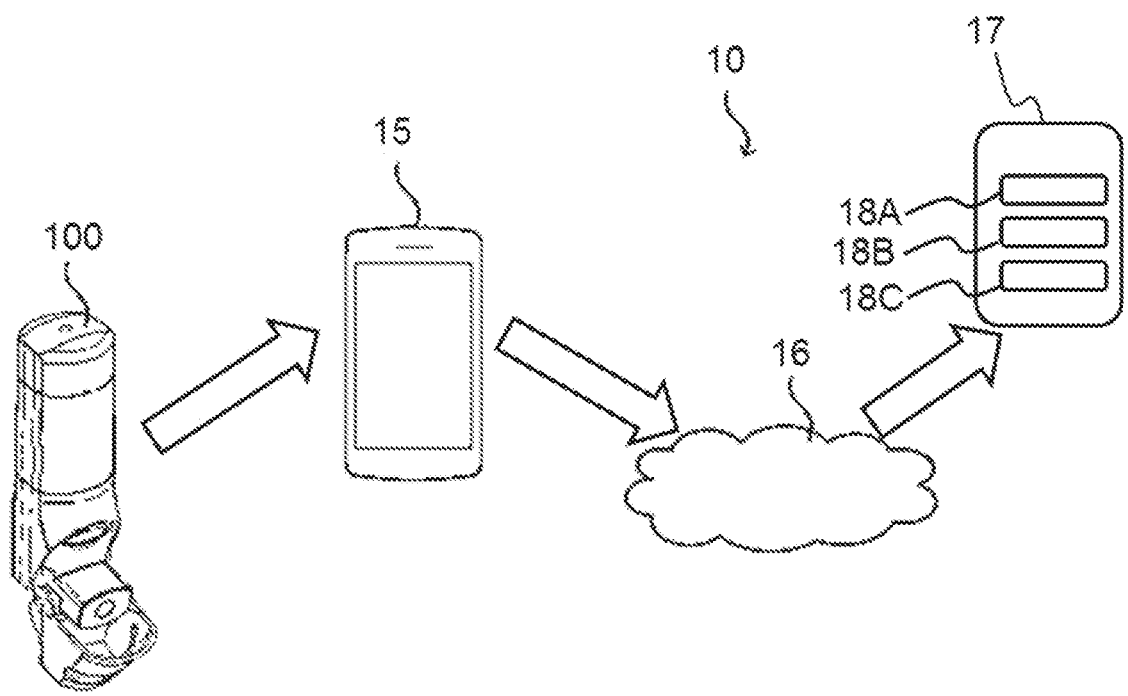
FIG. 2 shows a system according to another embodiment.

FIG. 2 shows a non-limiting example of a system 10 for determining a probability of a respiratory disease exacerbation in a subject. The weighted model, which may be alternatively termed a respiratory disease exacerbation risk prediction model, may be used to determine the probability and the result may then be provided to the subject, caregiver and/or healthcare provider.

The example system 10 includes the first inhaler 100, an external device 15 (e.g. a mobile device), a public and/or private network 16 (e.g. the Internet, a cloud network, etc.), and a personal data storage device 17. The external device 15 may, for example, include a smart phone, a personal computer, a laptop, a wireless-capable media device, a media streaming device, a tablet device, a wearable device, a Wi-Fi or wireless-communication-capable television, or any other suitable Internet Protocol-enabled device. For example, the external device 15 may be configured to transmit and/or receive RF signals via a Wi-Fi communication link, a Wi-MAX communications link, a Bluetooth® or Bluetooth® Smart communications link, a near field communication (NFC) link, a cellular communications link, a television white space (TVWS) communication link, or any combination thereof. The external device 15 may transfer data through the public and/or private network 16 to the personal data storage device 17.

The first inhaler 100 may include a communication circuit, such as a Bluetooth® radio, for transferring data to the external device 15. The data may include the abovementioned inhalation and parameter data.

The first inhaler 100 may also, for example, receive data from the external device 15, such as, for example, program instructions, operating system changes, dosage information, alerts or notifications, acknowledgments, etc.

The external device 15 may include at least part of the processor 14, and thereby process and analyze the inhalation and parameter data. For example, the external device 15 may process the data such as to determine the probability of the respiratory disease exacerbation, as represented by block 18A, and provide such information to the personal data storage device 17 for remote storage thereon.

In some non-limiting examples, the external device 15 may also process the data to identify no inhalation events, low inhalations events, good inhalation events, excessive inhalation events and/or exhalation events, as represented by block 18B. The external device 15 may also process the data to identify underuse events, overuse events and optimal use events, as represented by block 18C. The external device 15 may, for instance, process the data to estimate the number of doses delivered and/or remaining and to identify error conditions, such as those associated with a timestamp error flag indicative of failure of the subject to inhale a dose of the medicament which has been metered by the dose metering assembly. The external device 15 may include a display and software for visually presenting the usage parameters through a GUI on the display. The usage parameters may be stored as personalized data that may be stored for predicting future risk of exacerbations based on real-time data.

Although illustrated as being stored on the personal data storage device 17, in some examples, all or a portion of the probability of the respiratory disease exacerbation, as represented by block 18A, the no inhalation events, low inhalations events, good inhalation events, excessive inhalation events and/or exhalation events, as represented by block 18B, and/or the underuse events, overuse events and optimal use events, as represented by block 18C, may be stored on the external device 15.

Figure 3A:
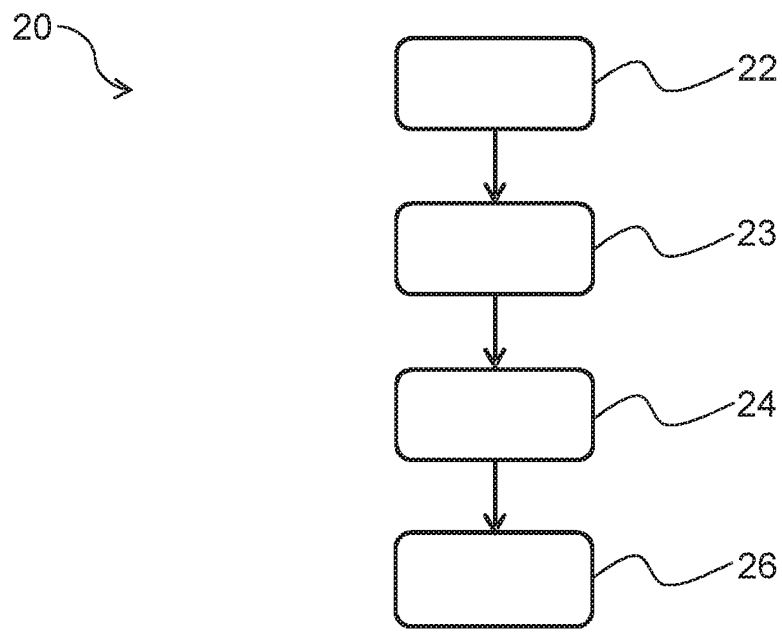
FIG. 3A shows a flowchart of a method according to an embodiment.

FIG. 3A shows a flowchart of a method 20 according to an embodiment. The method 20 may be performed by a system, such as the system 10 illustrated in FIGS. 1 and/or 2. For example, one or more of the first and/or second inhaler, the external device 15, and/or the personal data storage device 17 may be configured to perform the entirety of or a portion of the method 20. That is, any combination of the steps 22, 24, and 26 may be performed by any combination of the first inhaler, the second inhaler, the external device 15, and/or the personal data storage device 17. Further, it should be appreciated that the steps 22 and 24 may be performed in any chronological order.

The method 20 comprises determining 22 a number of rescue inhalations of a rescue medicament performed by a subject during a first time period. In step 24 a parameter relating to airflow during at least some, e.g. each, of the rescue and/or routine inhalations is measured. In step 26, a weighted model is used to determine the probability of the asthma exacerbation based on the number of rescue inhalations and the parameters. The model is weighted such that the number of rescue inhalations is more significant in the probability determination than the parameters.

Although not illustrated by in the method 20, the system 10 may be configured to notify the user if the probability of asthma exacerbation exceeds or is lower than a threshold. For example, the system 10 may be configured to determine whether the probability reaches or exceeds a predetermined upper threshold and/or reaches or is lower than a predetermined lower threshold. In response, the system 10 may be configured to treat the patient, for example, by initiating a switch (e.g. through a message to the patient's health care provider) of the patient's treatment regimen to a treatment regimen that is configured for higher (or lower) risk of asthma exacerbation than the original treatment regimen.

The system 10 may notify the user of their probability of asthma exacerbation through one or more techniques. For example, the system 10 may be configured to display a message on the display of the external device 15, send a message to a health-care provider or third party associated with the user, cause an indicator (e.g. light or speaker) of the inhaler 100 to notify the user, etc.

In the non-limiting example shown in FIG. 3A, the method further comprises receiving 23 an input of an indication of a status of the respiratory disease being experienced by the subject. This input may then be used to enhance the exacerbation prediction, as previously described.

In an embodiment, the method 20 comprises issuing a prompt to the user so that the user inputs the indication. The prompt may be issued based on the initial probability determined from the inhalation(s) and the inhalation parameter(s), but not on the indication. For example, the prompt may be issued based on the initial probability reaching or exceeding a predetermined threshold. In this manner, the user may be prompted by the system to input the indication on the basis of the initial probability signaling a potential impending exacerbation. By the user then inputting the indication, the (overall) probability which also takes account of the indication may assist to confirm or validate the initial probability.

Figure 3B:
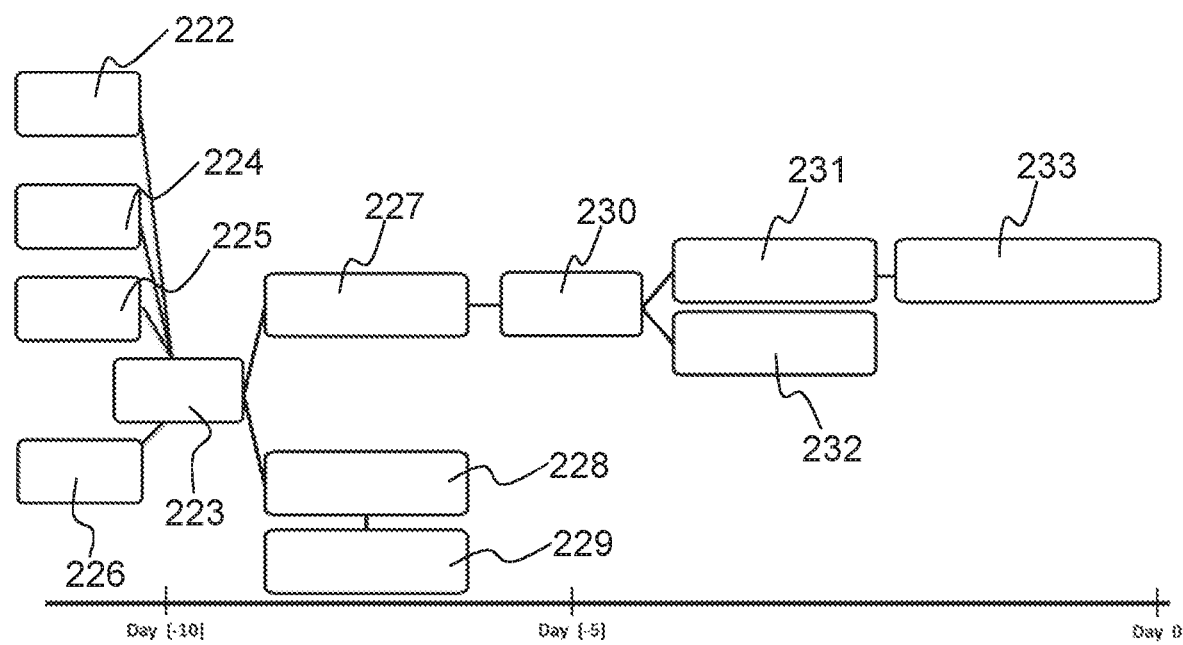
FIG. 3B shows a flowchart and timeline relating to a method according to another embodiment.

FIG. 3B shows a combined flowchart and timeline relating to an exemplary method. The timeline shows the day of a predicted exacerbation ("Day 0"), the fifth day prior to the exacerbation ("Day [−5]"), and the tenth day prior to the exacerbation ("Day [−10]").

In FIG. 3B, block 222 represents an inhaler use notification, which may be regarded as a notification concerning uses of a recue medicament and/or a maintenance medicament. Block 224 represents a flow notification, which corresponds to the parameter relating to airflow during inhalations. Block 225 represents a "use" and "flow" notification, which may regarded as a combined notification based on the inhaler uses and the inhalation parameter.

Block 226 represents a prediction notification. This prediction notification may be based on the initial probability determination described above. FIG. 3B shows a questionnaire launch in block 223 on Day [−10]. This launch may include issuing a prompt for the user to input the indication via the questionnaire. Block 227 represents the outcome of the questionnaire indicating that the exacerbation risk remains following the user input. This means that in block 230 the questionnaire is continued, or the user is asked to input the indication again or asked for further input relating to the status of their respiratory disease. Block 231 represents the scenario in which the exacerbation risk remains, e.g. following the overall probability determination described above, and in block 233 the exacerbation prediction notification continues.

Block 228 represents the scenario in which, following the questionnaire launch in block 223, the determined exacerbation risk returns, on the basis of the user-inputted notification, to the baseline. The risk notification is correspondingly terminated in block 229.

Similarly, block 232 represents the scenario in which, following the continued/further questionnaire completion in block 230, the exacerbation risk returns to the baseline. Whilst not shown in FIG. 3B (for the sake of simplicity of representation), the risk notification may be terminated following return of the exacerbation risk to the baseline in block 232.

More generally, the method 20 may further comprise providing a first inhaler for delivering the rescue medicament to the subject, the first inhaler having a use-detection system configured to determine the inhalation performed by the subject using the first inhaler.

The number of rescue inhalations may be determined and/or the parameter may be measured by the use-detection system and/or the sensor system respectively included in the first inhaler for delivering the rescue medication. The sensor system may alternatively or additionally measure the parameter related to airflow during a routine inhalation of a maintenance medicament using a second inhaler, as previously described.

The weighted model underpinning the method according to embodiments herein was the outcome of a clinical study, which will now be explained. The following should be regarded as an explanatory and non-limiting example.

Albuterol administered using the ProAir Digihaler marketed by Teva Pharmaceutical Industries was utilized in this 12-week, open-label study, although the results of the study are more generally applicable to other rescue medicaments delivered using other device types.

Patients 8 years old) with exacerbation-prone asthma were recruited to the study. Patients used the ProAir Digihaler (albuterol 90 mcg as the sulfate with a lactose carrier, 1-2 inhalations every 4 hours) as needed.

The electronics module of the Digihaler recorded each use, i.e. each inhalation, and parameters relating to airflow during each inhalation: peak inspiratory flow, volume inhaled, time to peak flow and inhalation duration. Data were downloaded from the inhalers and, together with clinical data, subjected to a machine-learning algorithm to develop models predictive of an impending exacerbation.

The diagnosis of a clinical asthma exacerbation (CAE) in this example was based on the American Thoracic Society/European Respiratory Society statement (H. K. Reddel et al., Am J Respir Crit Care Med. 2009, 180(1), 59-99). It includes both a "severe CAE" or a "moderate CAE."

A severe CAE is defined as a CAE that involves worsening asthma that requires oral steroid (prednisone or equivalent) for at least three days and hospitalization. A moderate CAE requires oral steroid (prednisone or equivalent) for at least three days or hospitalization.

Figure 8:
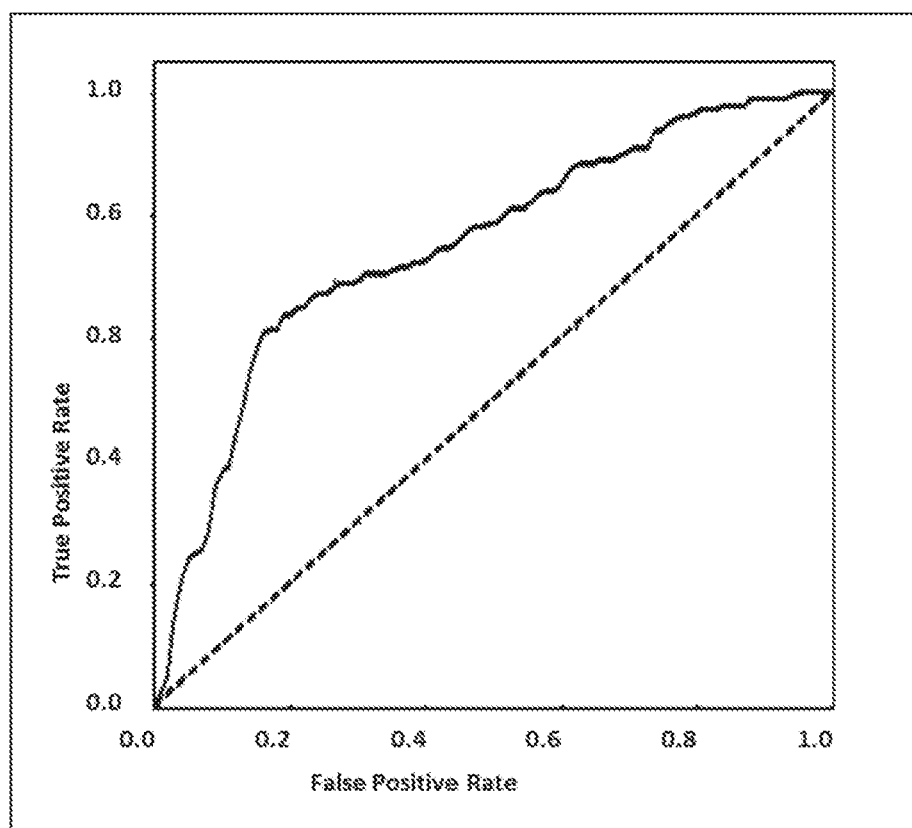
FIG. 8 shows a receiver operating characteristic (ROC) curve analysis of a model for determining the probability of an asthma exacerbation.

The generated model was evaluated by receiver operating characteristic (ROC) curve analysis, as will be explained in greater detail with reference to FIG. 8.

The objective and primary endpoint of the study was to explore the patterns and amount of albuterol use, as captured by the Digihaler, alone and in combination with other study data, such as the parameters relating to airflow during inhalation, physical activity, sleep, etc., preceding a CAE. This study represents the first successful attempt to develop a model to predict CAE derived from the use of a rescue medication inhaler device equipped with an integrated sensor and capable of measuring inhalation parameters.

Figure 4:
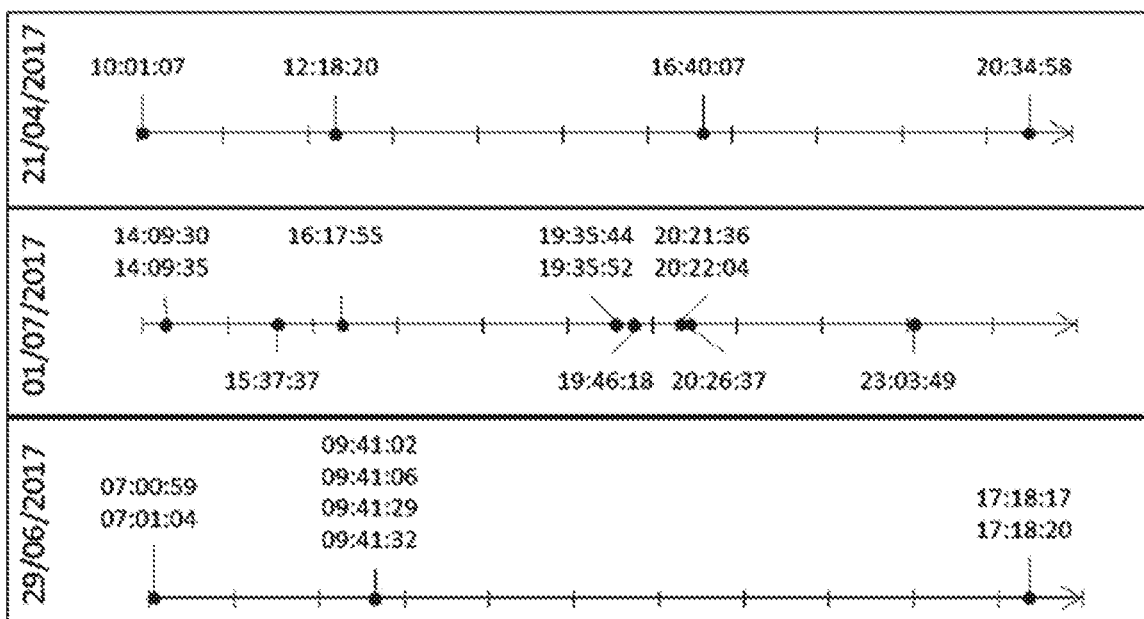
FIG. 4 shows timeline showing inhalations of a rescue medicament.

FIG. 4 shows three timelines showing different inhalation patterns recorded for three different patients by their respective Digihalers. The uppermost timeline shows that the patient in question takes one inhalation at a time. The lowermost timeline shows that the patient in question takes two or more consecutive inhalations in a session. The term "session" is defined in this context as a sequence of inhalations with no more than 60 seconds between consecutive inhalations. The middle timeline shows that the patient in question inhales in various patterns. Thus, as well as recording the number of rescue inhalations, the Digihaler is configured to record the pattern of use.

Figure 5:
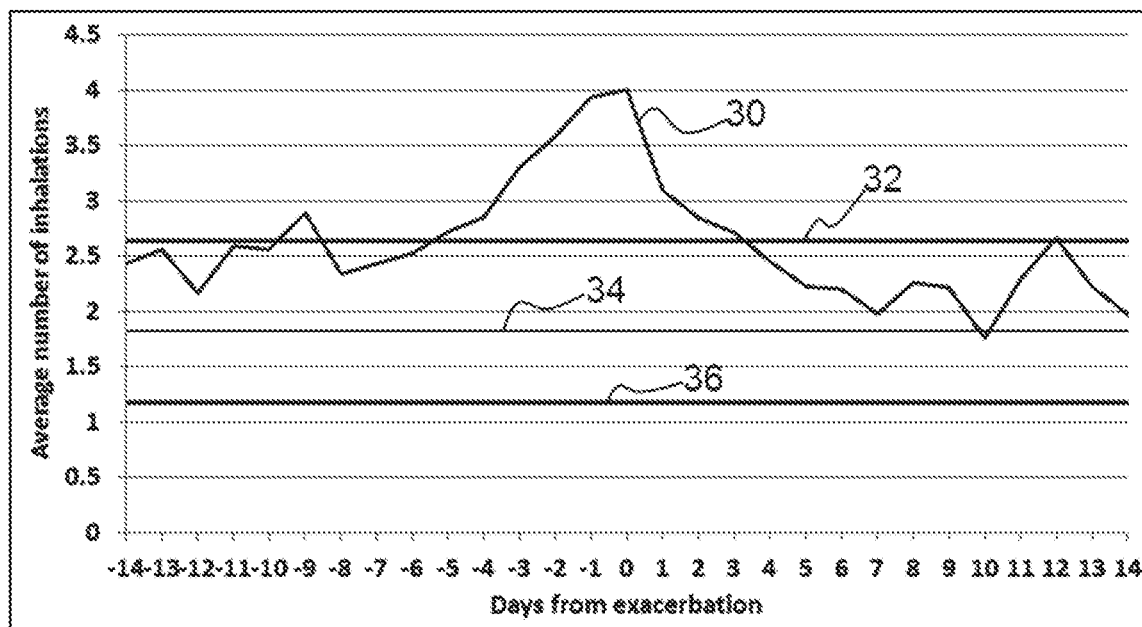
FIG. 5 shows a graph of average number of rescue inhalations versus days from an asthma exacerbation.

It was found that 360 patients performed valid inhalation from the Digihaler. These 360 patients were included in the analysis. Of these, 64 patients experienced a total of 78 CAEs. FIG. 5 shows a graph 30 of the average number of rescue inhalations versus days from an asthma exacerbation. FIG. 5 shows the data during a risk period which is 14 days either side of the day on which the exacerbation takes place. Line 32 corresponds to the average daily number of rescue inhalations during the risk period. Line 32 is higher on the y-axis than the baseline average daily number of rescue inhalations outside the risk period, represented by line 34. This is indicative of the average daily number of rescue inhalations increasing as the risk of an exacerbation increases. For reference, FIG. 5 further provides the baseline daily number of rescue inhalations for the patients which did not experience an exacerbation, represented by line 36.

Figure 6:
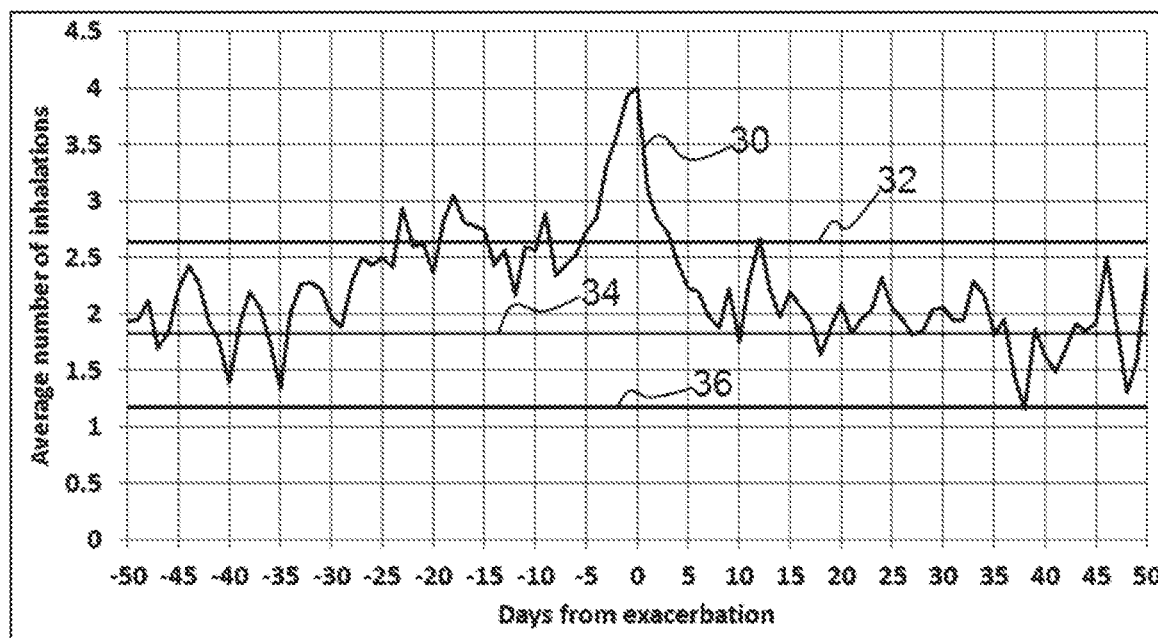
FIG. 6 shows another graph of average number of rescue inhalations versus number of days from an asthma exacerbation.

FIG. 6 shows another graph 30 of the average number of rescue inhalations versus number of days from an asthma exacerbation. FIG. 6 shows the data during a period which is 50 days either side of the day on which the exacerbation takes place. FIG. 6 shows the marked increase in rescue inhaler use as the day on which the exacerbation takes place approaches, as compared to the baseline average daily number of rescue inhalations outside the risk period, represented by line 34.

Figure 7:
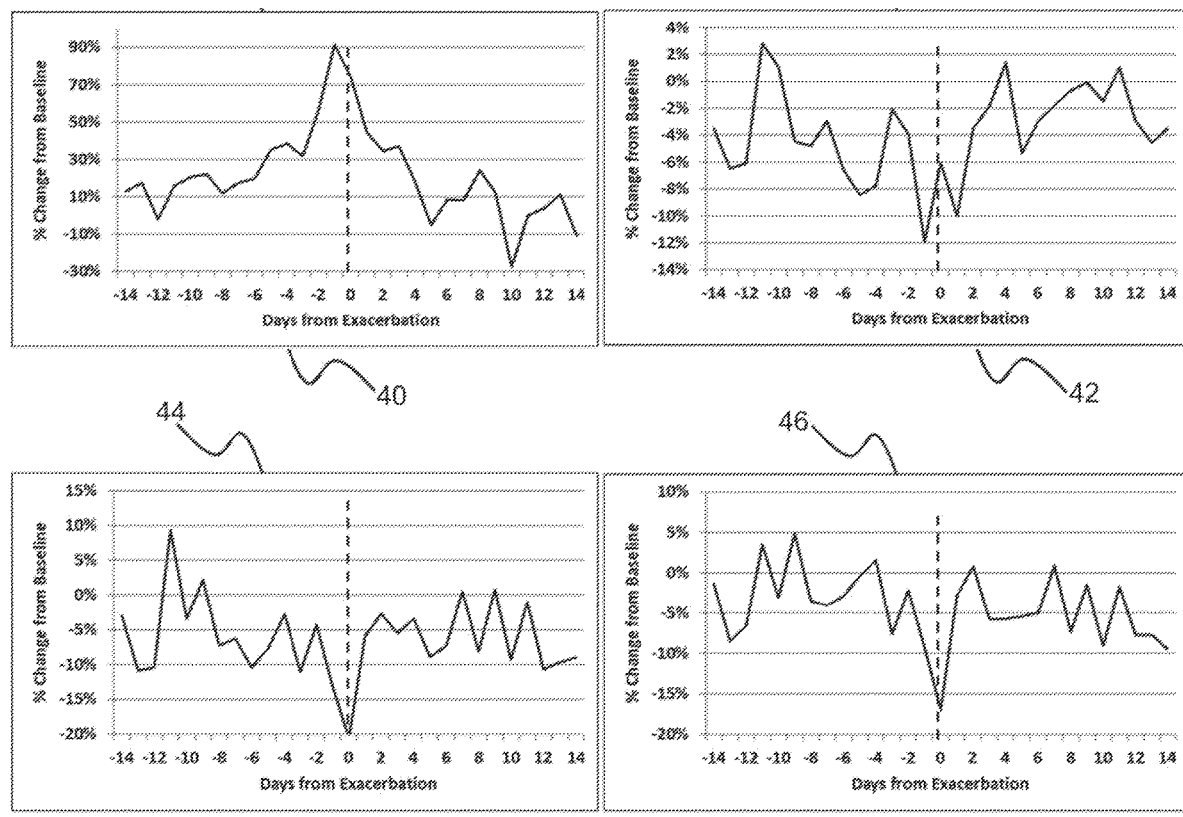
FIG. 7 shows four graphs showing the percentage change of number of rescue inhalations and various parameters relating to airflow relative to respective baseline values versus the number of days from an asthma exacerbation.

FIG. 7 shows four graphs showing the percentage change of number of rescue inhalations and various parameters relating to airflow relative to respective baseline values versus the number of days from an asthma exacerbation.

Graph 40 plots the percentage change in the number of rescue inhalations relative to the baseline (outside the risk period) versus days from the asthma exacerbation. The number of rescue inhalations was found to increase by 90% relative to the baseline immediately prior to the exacerbation.

Graph 42 plots the percentage change in the daily minimum peak inhalation flow relative to a baseline versus days from the asthma exacerbation. Graph 42 shows that the daily minimum peak inhalation flow generally decreases in the days leading up to the exacerbation. The daily minimum peak inhalation flow was found to decrease by 12% relative to the baseline immediately prior to the exacerbation.

Graph 44 plots the percentage change in the daily minimum inhalation volume relative to a baseline versus days from the asthma exacerbation. Graph 44 shows that the daily minimum inhalation volume generally decreases in the days leading up to the exacerbation. The daily minimum inhalation volume was found to decrease by 20% relative to the baseline immediately prior to the exacerbation.

Graph 46 plots the percentage change in the daily minimum inhalation duration relative to a baseline versus days from the asthma exacerbation. Graph 46 shows that the daily minimum inhalation duration generally decreases in the days leading up to the exacerbation. The daily minimum inhalation duration was found to decrease by between 15% and 20% relative to the baseline immediately prior to the exacerbation.

In the construction of a first weighted predictive model, it was found that the strongest predictive factor of the asthma exacerbation, particularly during the period of 5 days before a CAE, was the average number of rescue inhalations per day. The parameter relating to air flow, i.e. peak inhalation flow, inhalation volume and/or inhalation duration, was also found to have significant predictive value.

In the first weighted predictive model, the most significant features in determining the probability of an asthma exacerbation were found to be: the number of rescue inhalations 61%; inhalation trends 16%; peak inhalation flow 13%; inhalation volume 8%; and night albuterol use 2%. Such inhalation features were collected by the Digihaler, which recorded peak inhalation flow, time to peak inhalation flow, inhalation volume, inhalation duration, night-time usage, and trends of these parameters over time.

Inhalation trends are artificially created or "engineered" parameters, such as the percentage change in inhalation volume today compared to the last three days. Another example is the change in the number of rescue inhalations today compared to the last three days. The respective trend is not, in these examples, the inhalation volume or the number of rescue inhalations per se, but respective variations on these.

On the basis of the above results, the first weighted predictive model was developed to determine the probability of the asthma exacerbation. The supervised machine learning technique, Gradient Boosting Trees, was used to solve the classification problem (yes/no exacerbation in the upcoming x days (exacerbation period)).

The Gradient Boosting Trees technique is well-known in the art. See: J. H. Friedman, Computational Statistics & Data Analysis 2002, 38(4), 367-378; and J. H. Friedman et al., The Annals of Statistics 2000, 28(2), 337-407. It produces a prediction model in the form of an ensemble (multiple learning algorithms) of base prediction models, which are decision trees (a tree-like model of decisions and their possible consequences). It builds a single strong learner model in an iterative fashion by using an optimization algorithm to minimize some suitable loss function (a function of the difference between estimated and true values for an instance of data). The optimization algorithm uses a training set of known values of the response variable (yes/no exacerbation in the upcoming x days) and their corresponding values of predictors (the list of the features and engineered features) to minimize the expected value of the loss function. The learning procedure consecutively fits new models to provide a more accurate estimate of the response variable.

Table A provides an exemplary list of factors included in the first weighted predictive model, together with their relative weighting to each other.

TABLE A

List of factors.

| | Feature | Weighting |
|---|---|---|
| Number of inhalations | Normalized* number of rescue inhalations (last 3 days) | 0.1631 |
| | Average number of daily rescue inhalations in the last 5 days | 0.0876 |
| | Normalized* number of rescue inhalations today | 0.0847 |
| | Normalized* number of inhalation events today | 0.0668 |
| | Maximal number of daily rescue inhalations in the last 5 days | 0.0604 |
| | Absolute number of rescue inhalations in the last 3 days | 0.0556 |
| | Number of rescue inhalations 3 days ago | 0.0442 |
| | Number of rescue inhalations 4 days ago | 0.0439 |
| | Number of rescue inhalations 2 days ago | 0.0390 |
| | Absolute number of inhalation events today | 0.0337 |
| | % of change in number of rescue inhalations today, compared to last 3 days | 0.0309 |
| | Number of rescue inhalations yesterday | 0.0301 |
| | Absolute number of rescue inhalations today | 0.0263 |
| | Absolute number of rescue inhalations during night time in the last 3 days | 0.0180 |
| | Total weighting: number of inhalations | 0.7843 |
| Inhalation parameters | % of change in inhalation peak flow today, compared to last 3 days | 0.0824 |
| | % of change in inhalation volume today, compared to last 3 days | 0.0500 |
| | Normalized* inhalation peak flow today | 0.0461 |
| | Normalized* inhalation volume today | 0.0374 |
| | Total weighting: inhalation parameters | 0.2159 |

*The term "normalized" means relative to the respective baseline

Whilst the key factor in the predictive model for determining the probability of an impending asthma exacerbation is the number of rescue inhalations, including trends relating to the number of rescue inhalations, the predictive model was strengthened by supplementing this with the parameter relating to airflow during inhalation. FIG. 8 shows a receiver operating characteristic (ROC) curve analysis of the model, which assesses the quality of the model by plotting the true positive rate against the false positive rate. This first weighted predictive model predicted an impending exacerbation over the subsequent 5 days with an AUC value of 0.75 using the relevant features described above. The AUC value is 0.69 when using features based on number of rescue inhalations only.

Accordingly, the parameter relating to airflow during inhalation, in common with the factors other than the number of rescue inhalations, may represent a significant factor in improving the accuracy with which the probability of an asthma exacerbation may be determined, in spite of exerting less overall influence on the probability than the number of rescue inhalations.

A second weighted predictive model was developed using the same data, in an effort to improve on the first weighted predictive model. Biometric parameters were included in the modelling. In particular, case report form (CRF) data, such as medical history, body mass index (BMI), and blood pressure, were combined with Digihaler data and subjected to the machine learning algorithm in order to refine the predictive model.

Algorithms were trained on patient-specific inhalation information collected from Digihalers, as well as age, BMI, blood pressure, and the number of exacerbations and hospitalizations in the past 12 months. Baseline features and features prior to prediction, comparison between the two, and trends of changes in these features were subjected to supervised machine learning algorithms. A 4-fold cross validation technique was used to compare performance metrics and gradient boosting trees were chosen as the most suitable algorithm. As before, the generated model was evaluated by receiver operating characteristic area under curve (ROC AUC) analysis.

Table B provides an exemplary list of factors included in the second weighted predictive model, together with their relative weighting to each other.

TABLE B

List of factors.

| | Feature | Weighting |
|---|---|---|
| Number of inhalations | Number of rescue inhalations (last 4 days) | 0.47 |
| | Number of rescue inhalations during night time | 0.06 |
| | Comparison to the baseline number of inhalations | 0.04 |
| | Total weighting: number of inhalations | 0.57 |
| Inhalation parameters | Comparison to baseline flow parameters | 0.14 |
| | Flow parameters (last 4 days) | 0.11 |
| | Baseline flow parameters | 0.06 |
| | Trends of flow parameters prior to exacerbation prediction | 0.04 |
| | Total weighting: inhalation parameters | 0.35 |
| Biometric parameter | Exacerbations and medical history | 0.05 |
| | Body mass index | 0.02 |
| | Systolic blood pressure | 0.01 |
| | Total weighting: biometric parameter | 0.08 |

This second weighted predictive model predicted an impending exacerbation over the subsequent 5 days with an AUC value of 0.83. The second weighted predictive model had a sensitivity of 68.8% and a specificity of 89.1%. Thus, this second weighted predictive model represented an improved asthma exacerbation predictive model than the first weighted predictive model described above, which had an AUC of 0.75. The additional refinement of the second weighted predictive model may be at least partly ascribed to the inclusion of the biometric parameter.

More generally, the first time period over which the number of rescue inhalations is to be determined may be 1 to 15 days, such as 3 to 8 days. Monitoring the number of rescue inhalations over such a first time period may be particularly effective in the determination of the probability of the asthma exacerbation.

When the parameter includes the peak inhalation flow, the method 20 may further comprise determining a peak inhalation flow, such as a minimum or average peak inhalation flow from peak inhalation flows measured for inhalations performed during a second time period. The term "second" in relation to the second time period is to distinguish the period for sampling the peak inhalation flows from the first time period during which the number of rescue inhalations are sampled. The second time period may at least partially overlap with the first time period, or the first and second time periods may be concurrent.

The step 26 of determining the probability of the asthma exacerbation may thus be partially based on the minimum or average peak inhalation flow. The second time period may be, for instance, 1 to 5 days, such as 1 day. The second time period may be selected according to the time required to gather peak inhalation flow data of suitable indicative value, in a manner analogous to the considerations explained above in relation to the first time period.

The determining the probability of the asthma exacerbation may, for example, be partially based on a change in the minimum or average peak inhalation flow relative to a baseline peak inhalation flow, as per graph 42 of FIG. 7.

For enhanced accuracy in predicting the exacerbation, the change in the minimum or average peak inhalation flow relative to the baseline may be, for instance, 10% or more, such as 50% or more or 90% or more. The baseline may, for example, be determined using daily minimum peak inhalation flows measured over a period in which no exacerbation has taken place, for example for 1 to 20 days. Alternatively or additionally, the minimum or average peak inhalation flow may be assessed relative to an absolute value.

The method 20 may further comprise determining an inhalation volume, such as a minimum or average inhalation volume from inhalation volumes measured for inhalations performed during a third time period. The term "third" in relation to the third time period is to distinguish the period for sampling the inhalation volumes from the first time period during which the number of rescue inhalations are sampled, and the second time period during which the peak inhalation flow data are sampled. The third period may at least partially overlap with the first time period and/or the second time period, or the third time period may be concurrent with at least one of the first time period and the second time period.

The step 26 of determining the probability of the asthma exacerbation may thus be partially based on the minimum or average inhalation volume. The third time period may be, for instance, 1 to 5 days, such as 1 day. The third time period may be selected according to the time required to gather minimum inhalation volume data of suitable indicative value, in a manner analogous to the considerations explained above in relation to the first time period.

The determining the probability of the asthma exacerbation may, for example, be partially based on a change in the minimum or average inhalation volume relative to a baseline inhalation volume, as per graph 44 of FIG. 7.

For enhanced accuracy in predicting the exacerbation, the change in the minimum or average inhalation volume relative to the baseline may be, for instance, 10% or more, such as 50% or more or 90% or more. The baseline may, for example, be determined using daily minimum inhalation volumes measured over a period in which no exacerbation has taken place, for example for 1 to 10 days. Alternatively or additionally, the minimum or average inhalation volume may be assessed relative to an absolute value.

The method 20 may further comprise determining an inhalation duration, such as a minimum or average inhalation duration from inhalation durations measured for inhalations over a fourth time period. The term "fourth" in relation to the fourth time period is to distinguish the period for sampling the minimum inhalation durations from the first time period during which the number of rescue inhalations are sampled, the second time period during which the peak inhalation flow data are sampled, and the third time period during which the inhalation volume data are sampled. The fourth time period may at least partially overlap with the first time period, the second time period and/or the third time period, or the fourth time period may be concurrent with at least one of the first time period, the second time period and the third time period.

The step 26 of determining the probability of the asthma exacerbation may thus be partially based on the minimum or average inhalation duration. The fourth time period may be, for instance, 1 to 5 days, such as 1 day. The fourth time period may be selected according to the time required to gather minimum inhalation duration data of suitable indicative value, in a manner analogous to the considerations explained above in relation to the first time period.

The determining the probability of the asthma exacerbation may, for example, be partially based on a change in the minimum or average inhalation duration relative to a baseline inhalation duration as per graph 46 of FIG. 7.

For enhanced accuracy in predicting the exacerbation, the change in the minimum or average inhalation duration relative to the baseline may be, for instance, 10% or more, such as 50% or more or 90% or more. The baseline may, for example, be determined using daily minimum inhalation durations measured over a period in which no exacerbation has taken place, for example for 1 to 20 days. Alternatively or additionally, the minimum or average inhalation duration may be assessed relative to an absolute value.

A further clinical study was undertaken in order to better understand the factors influencing prediction of COPD exacerbation. The following should be regarded as an explanatory and non-limiting (comparative) example.

Albuterol administered using the ProAir Digihaler marketed by Teva Pharmaceutical Industries was utilized in this 12-week, multicenter, open-label study, although the results of the study are more generally applicable to other rescue medicaments delivered using other device types.

The Digihaler enabled recording of: total number of inhalations, maximal inhalation flow, time to maximal inhalation flow, inhalation volume, and inhalation duration. The data were downloaded from the electronics module of the Digihaler at the end of the study.

An acute COPD exacerbation (AECOPD) was the primary outcome measure of this study. In this study, an AECOPD is an occurrence of either a "severe AECOPD" or a "moderate AECOPD." "Mild AECOPD" was not used as a measure of AECOPD in this study.

Severe AECOPD is defined as an event that involves worsening respiratory symptoms for at least two consecutive days requiring treatment with systemic corticosteroids (SCS, at least 10 mg prednisone equivalent above baseline) and/or systemic antibiotics and a hospitalization for AECOPD.

Moderate AECOPD is defined as an event that involves worsening respiratory symptoms for at least two consecutive days requiring treatment with SCS (at least 10 mg prednisone equivalent above baseline), and/or systemic antibiotics, and an unscheduled encounter (such as a phone call, an office visit, an urgent care visit, or an emergency care visit) for a AECOPD, but not a hospitalization.

Patients (40 years old) with COPD were recruited to the study. Patients used the ProAir Digihaler (albuterol 90 mcg as the sulfate with a lactose carrier, 1-2 inhalations every 4 hours) as needed.

The inclusion criteria required that the patient is on a SABA plus at least one of the following: LABA, ICS/LABA, LAMA, or LABA/LAMA; suffered least one episode of moderate or severe AECOPD over the past 12 months before screening; is able to demonstrate appropriate use of albuterol from the Digihaler; and is willing to discontinue all other rescue or maintenance SABA or short-acting anti-muscarinic agents and replace them with the study-provided Digihaler for the duration of the trial.

Patients were excluded from the study if they had any clinically significant medical condition (treated or untreated) that, in the opinion of the investigator, would interfere with participation in the study; any other confounding underlying lung disorder other than COPD; used an investigational drug within 5 half-lives of it being discontinued, or 1 month of visit 2, whichever is longer; had congestive heart failure; were pregnant or were lactating, or had plans to become pregnant during the study.

Two subsets of ca. 100 patients were required to wear an accelerometer either on the ankle to measure physical activity (Total Daily Steps, TDS) or on the wrist to measure sleep disturbance (Sleep Disturbance Index, SDI).

The general factors of interest relating to rescue medicament use were:

(1) total number of inhalations in the days preceding the peak of a AECOPD
(2) number of days prior to the peak of a AECOPD when albuterol use increased, and
(3) number of albuterol uses in the 24 hours preceding a AECOPD.

Approximately 400 patients were enrolled. This provided 366 evaluable patients which completed the study. 336 valid inhalations of the Digihaler were recorded. Further details in this respect are provided in Table 1.

TABLE 1

| Analysis group, n (%) | Total |
|---|---|
| Screened | 423 |
| Screen failure | 18 |
| Enrolled | 405 (100) |
| Enrolled but did not use ABS eMDPI | 15 (4) |
| Used ABS eMDPI at least once | 390 (96) |
| ITT analysis set | 405 (100) |
| Ankle accelerometry analysis set | 96 (24) |
| Wrist accelerometry analysis set | 85 (21) |
| Completed study | 366 (90) |
| Discontinued study | 39 (10) |
| Adverse event | 8 (2) |
| Death | 2 (<1) |
| Withdrawal by subject | 14 (3) |
| Non-compliance with study drug | 1 (<1) |
| Pregnancy | 0 |
| Lost to follow-up | 3 (<1) |
| Lack of efficacy | 3 (<1) |
| Protocol deviation | 5 (1) |
| Other | 3 (<1) |

98 of the patients which completed the study suffered AECOPD events and used the Digihaler. A total of 121 moderate/severe AECOPD events were recorded. Further details are provided in Table 2.

TABLE 2

| | AECOPD: "No" | AECOPD: "Yes, Moderate" | AECOPD: "Yes, Severe" | AECOPD: All | Overall |
|---|---|---|---|---|---|
| Number of Patients | 287 | 85 | 24 | 109 | 396 |
| Number of AECOPD events | 0 | 95 | 26 | 121 | |
| Number of patients with at least 1 AECOPD event | 0 | 85 | 24 | 109 | |
| Mean number of days Digihaler used by Patients | 43.9 | 51.1 | 31.8 | 46.9 | 44.7 |
| Min, max number of days Digihaler used by Patients | 0, 92 | 0, 90 | 0, 85 | 0, 90 | 0, 92 |
| Mean daily albuterol exposure (μg) of Patients | 211.29 | 273.61 | 233.06 | 264.68 | 225.99 |
| Min, max daily albuterol exposure (μg) of Patients | 0.0, 1534.6 | 0.0, 1157.0 | 0.0, 1243.8 | 0.0, 1243.8 | 0.0, 1534.6 |

For 366 patients which completed the study: 30 (8%) patients did not use inhaler at all; 268 (73%) had a daily average of up to 5 inhalations; and 11 (3%) had a daily average greater than 10 inhalations.

Figure 9:
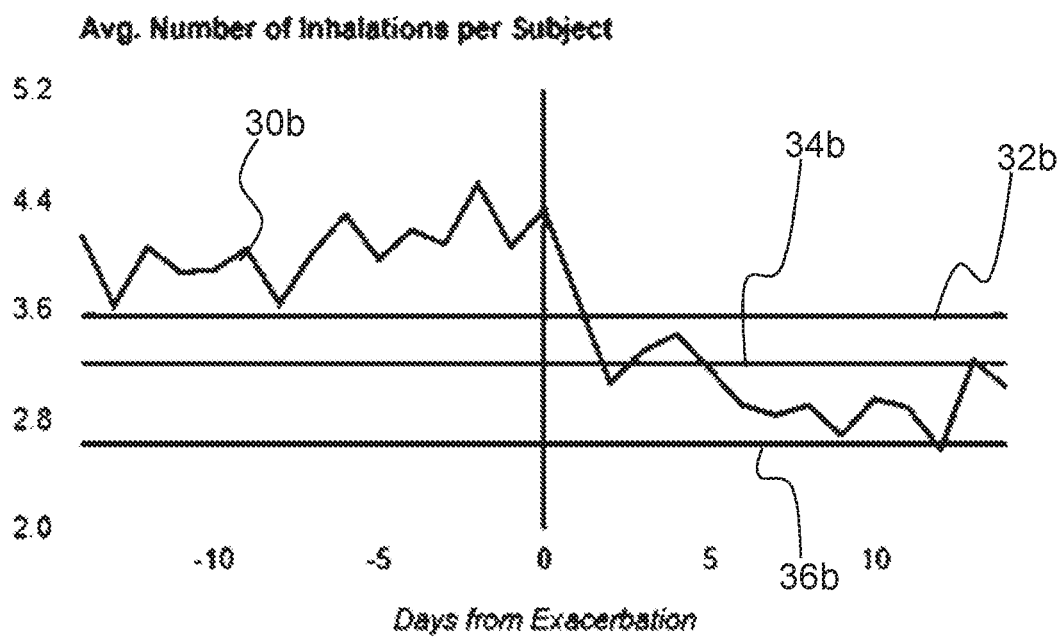
FIG. 9 shows a graph of average number of rescue inhalations versus number of days from a COPD exacerbation.

FIG. 9 shows a graph 30b of the average number of rescue inhalations per subject versus days from a COPD exacerbation. FIG. 9 shows the data during a risk period which is 14 days either side of the day on which the exacerbation takes place. Line 32b corresponds to the average daily number of rescue inhalations during the risk period. Line 32b is higher on the y-axis than the baseline average daily number of rescue inhalations outside the risk period, represented by line 34b. This is indicative of the average daily number of rescue inhalations increasing as the risk of an exacerbation increases. For reference, FIG. 9 further provides the baseline daily number of rescue inhalations for the patients which did not experience an exacerbation, represented by line 36b.

Figure 10:
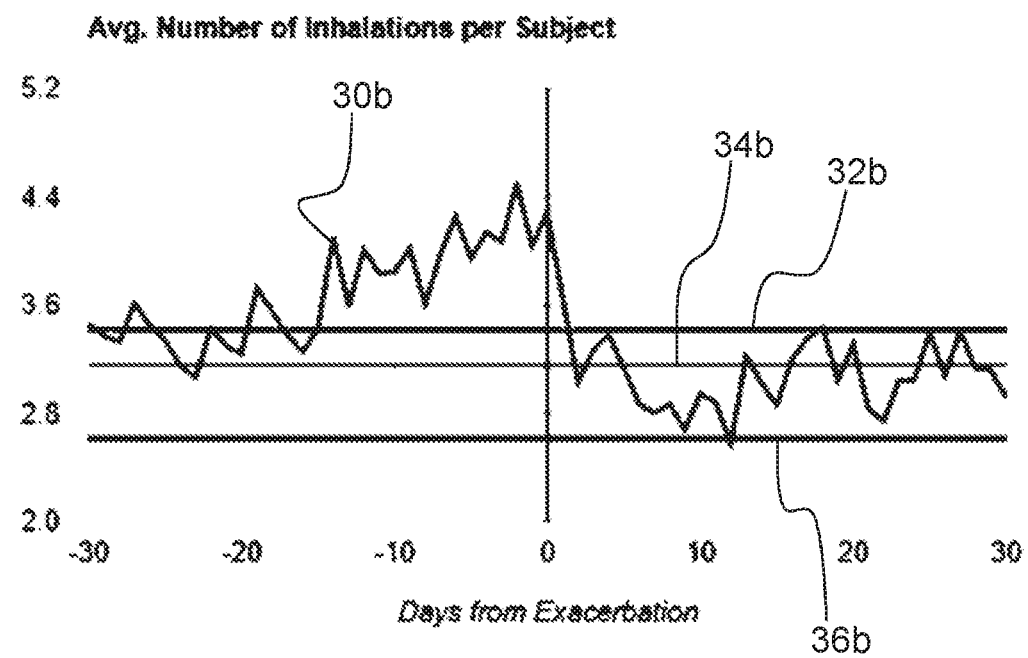
FIG. 10 shows another graph of average number of rescue inhalations versus number of days from a COPD exacerbation.

FIG. 10 shows another graph 30b of the average number of rescue inhalations per subject versus number of days from a COPD exacerbation. FIG. 10 shows the data during a period which is 30 days either side of the day on which the exacerbation takes place. FIG. 10 shows the marked increase in rescue inhaler use as the day on which the exacerbation takes place approaches, as compared to the baseline average daily number of rescue inhalations outside the risk period, represented by line 34b.

The data show an increase in the number of rescue medicament inhalations about two weeks prior to the exacerbation. There is a further smaller increase about one week prior to the exacerbation. Table 3 provides further details in relation to the association between increased rescue medicament use and AECOPD.

TABLE 3

| Variable Statistic | AECOPD: "Yes" (N = 109) | AECOPD: "No" (N = 287) | Odds ratio[2] (95% CI) | P value | C-statistic |
|---|---|---|---|---|---|
| Patients with albuterol use >20% increase from baseline in a single day[1]: YES | 97 (89%) | 223 (78%) | 2.32 (1.198, 4.493) | 0.0126 | 0.56 |
| Patients with albuterol use >20% increase from baseline in a single day: NO | 12 (11%) | 64 (22%) | | | |

[1]For patients who experienced an AECOPD event, the albuterol use is prior to the symptom peak of the event. For patients who experienced multiple events, only the first one is included in the analysis. Baseline albuterol use is defined as the average of inhalations during the first 7 days in the study. If no inhalations occurred during the first 7 days, the first available inhalation after day 7 is used. If no inhalation occurred during the entire study, the baseline is 0 (zero).
[2]All inferential statistics, odds ratio, p value, and C-statistics for goodness of fit were estimated from a logistic regression model with increased albuterol use status and baseline albuterol use as the explanatory variables. An odds ratio of greater than 1 indicates that patients whose daily albuterol use ever exceeded 20% more than the baseline are more likely to experience an AECOPD event than those whose albuterol use never exceeded 20% more than the baseline. Patients who experienced AECOPD during study day 1 through study day 7 are excluded from the analysis.

Figure 11:
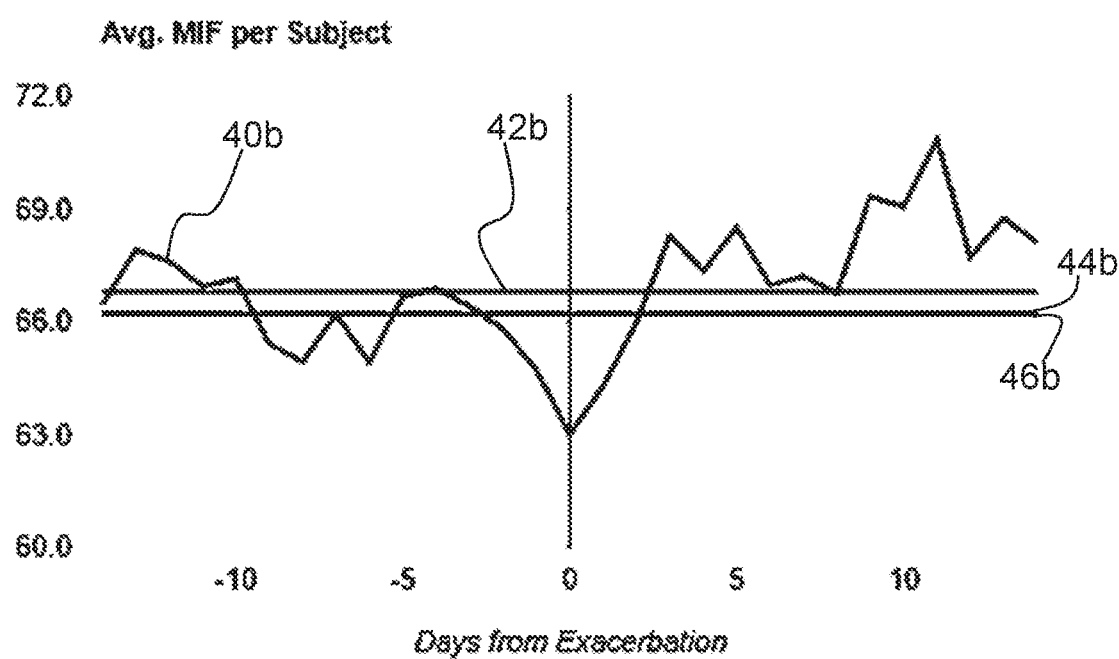
FIG. 11 shows a graph of mean peak inhalation flow (L/min) versus days from a COPD exacerbation.

FIG. 11 shows a graph 40b of the average (mean) peak inhalation flow per subject versus days from a COPD exacerbation. FIG. 11 shows the data during a risk period which is 14 days either side of the day on which the exacerbation takes place. Line 42b corresponds to the average peak inhalation flow during the risk period. Line 42b is slightly higher on the y-axis than the baseline average peak inhalation flow outside the risk period, represented by line 44b, although this difference is not thought to be significant. FIG. 11 further provides the baseline average peak inhalation flow for the patients which did not experience an exacerbation, represented by line 46b.

Figure 12:
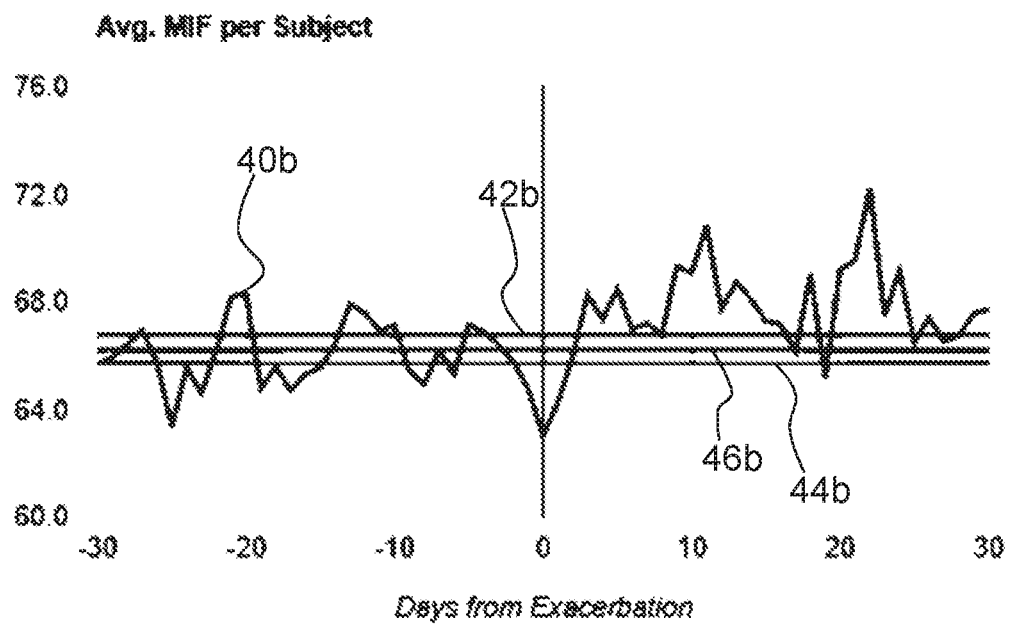
FIG. 12 shows another graph of mean peak inhalation flow (L/min) versus days from a COPD exacerbation.

FIG. 12 shows another graph 60b of the average (mean) peak inhalation flow per subject versus days from a COPD exacerbation. FIG. 12 shows the data during a period which is 30 days either side of the day on which the exacerbation takes place. FIG. 12 shows a relatively steady and low average peak inhalation flow prior to the exacerbation.

Figure 13:
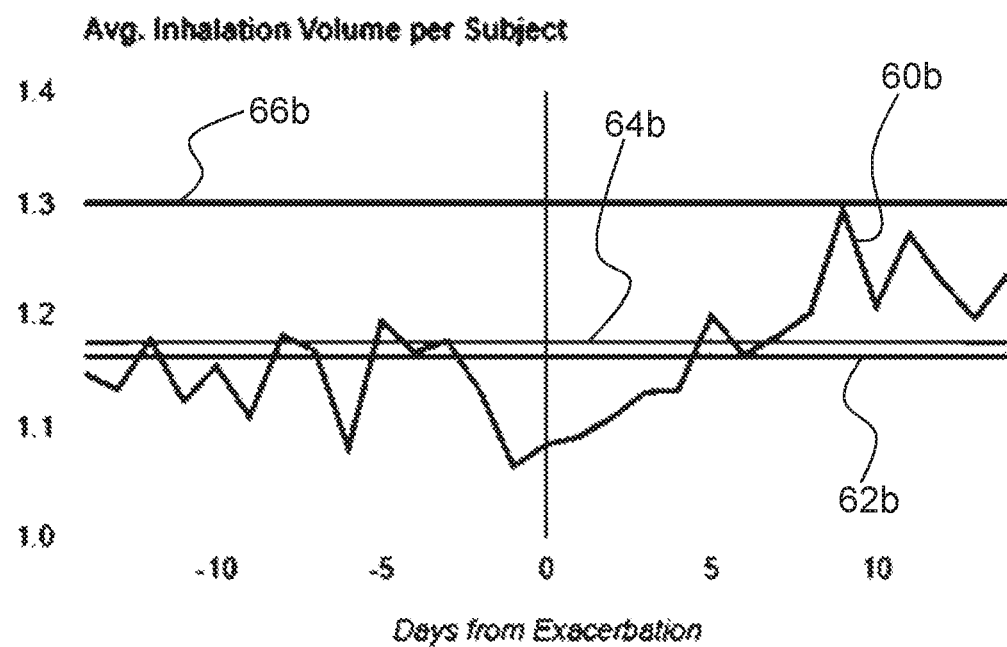
FIG. 13 shows a graph of mean inhalation volume (L) versus days from a COPD exacerbation.

FIG. 13 shows a graph 60b of the average inhalation volume per subject versus days from a COPD exacerbation. FIG. 13 shows the data during a risk period which is 14 days either side of the day on which the exacerbation takes place. Line 62b corresponds to the average inhalation volume during the risk period. Line 62b is lower on the y-axis than the baseline average inhalation volume outside the risk period, represented by line 64b. FIG. 13 further provides the baseline average inhalation volume for the patients which did not experience an exacerbation, represented by line 66b.

Figure 14:
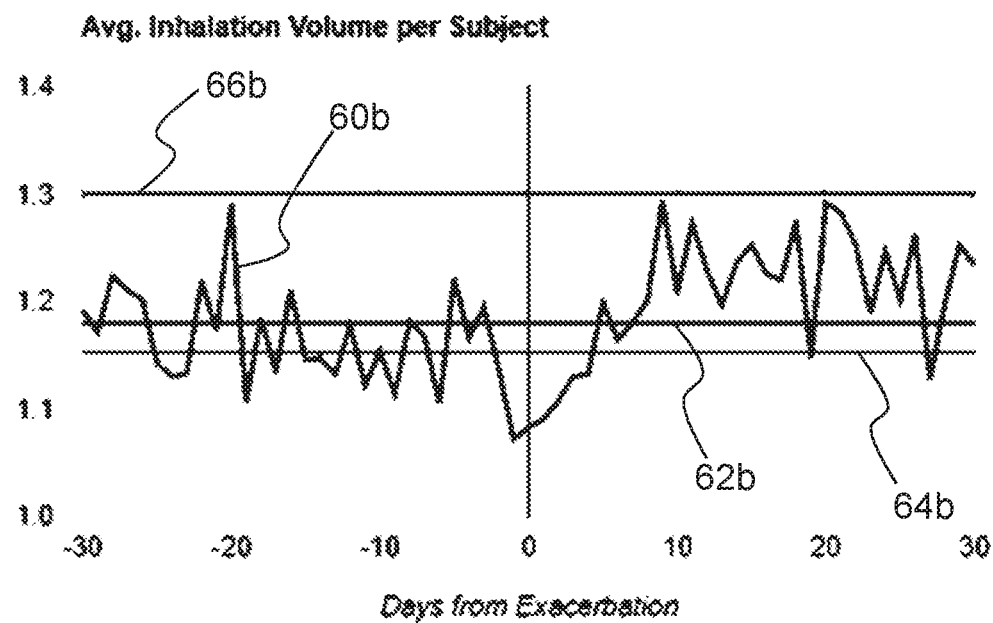
FIG. 14 shows another graph of mean inhalation volume (L) versus days from a COPD exacerbation.

FIG. 14 shows another graph 60b of the average inhalation volume per subject versus days from a COPD exacerbation. FIG. 14 shows the data during a period which is 30 days either side of the day on which the exacerbation takes place.

Figure 15:
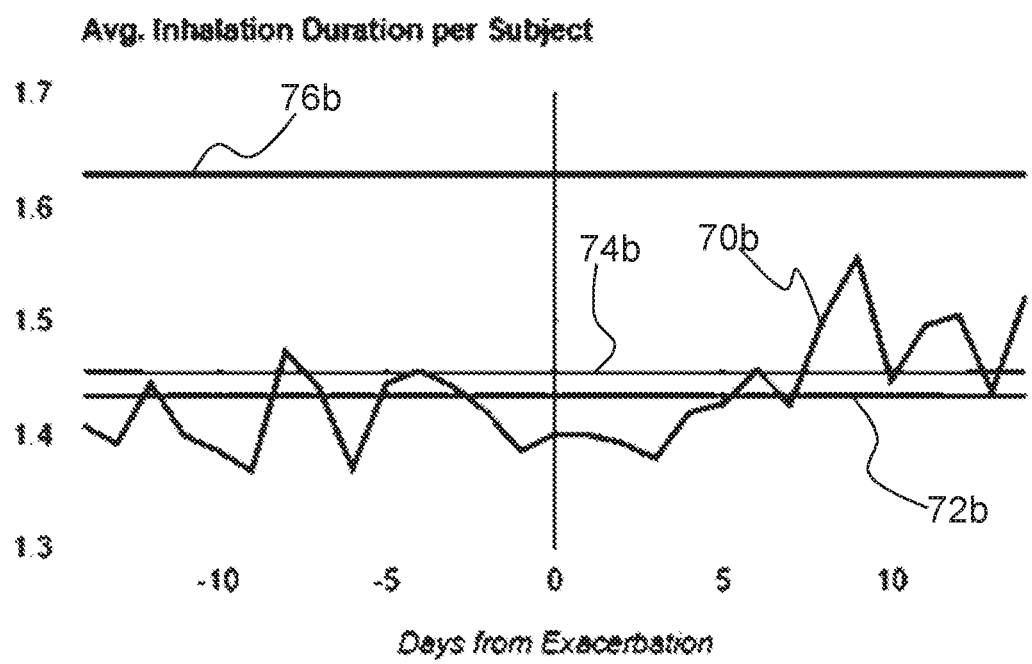
FIG. 15 shows a graph of mean inhalation duration (s) versus days from a COPD exacerbation.

FIG. 15 shows a graph 70b of the average inhalation duration per subject versus days from a COPD exacerbation. FIG. 15 shows the data during a risk period which is 14 days either side of the day on which the exacerbation takes place. Line 72b corresponds to the average inhalation duration during the risk period. Line 72b is lower on the y-axis than the baseline average inhalation duration outside the risk period, represented by line 74b. FIG. 15 further provides the baseline average inhalation duration for the patients which did not experience an exacerbation, represented by line 76b.

Figure 16:
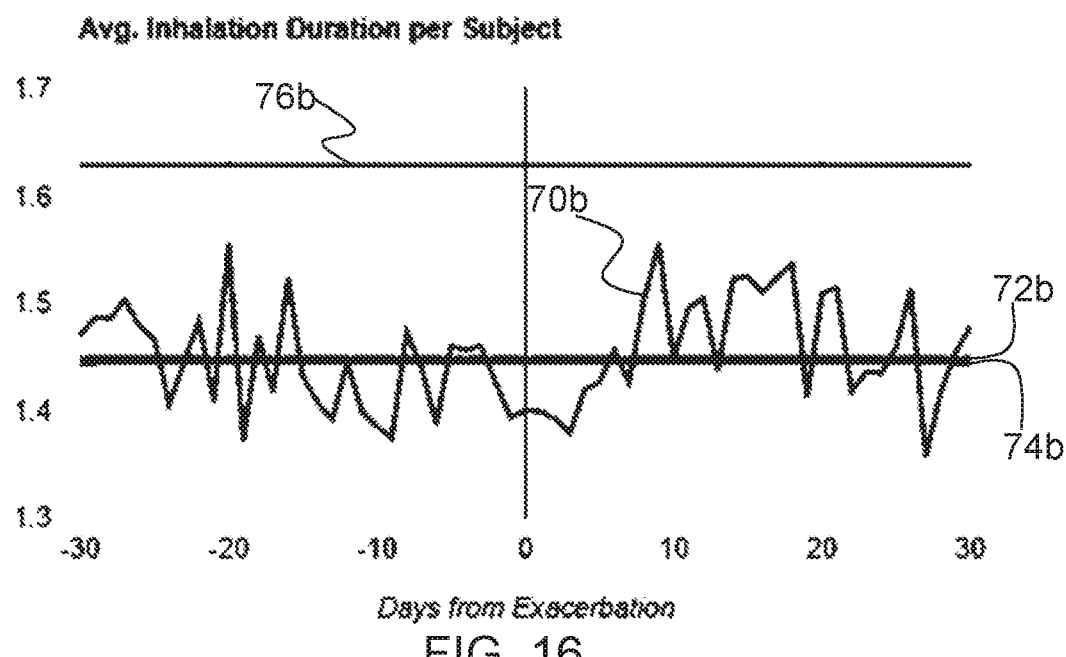
FIG. 16 shows another graph of mean inhalation duration (s) versus days from a COPD exacerbation.

FIG. 16 shows another graph 70b of the average inhalation duration per subject versus days from a COPD exacerbation. FIG. 16 shows the data during a period which is 30 days either side of the day on which the exacerbation takes place.

FIGS. 13-16 reveal a relatively long term (evident over about 30 days) linear decrease in inhalation volume and duration prior to AECOPD.

Table 4 compares the inhalation parameters and rescue medicament usage recorded for patients during and outside the ±14-day AECOPD window, and for patients which did not experience an AECOPD.

TABLE 4

Inhalation characteristics and rescue medicament use during and outside the ± 14-day AECOPD window and in patients without AECOPDs

| | Patients with AECOPD(s), n = 98 | | Patients without AECOPD (n = 242) |
|---|---|---|---|
| | During ± 14-day AECOPD window | Outside ± 14-day AECOPD window | |
| Mean peak inhalation flow, L/min (SD) | 66.79 (16.02) | 66.17 (15.89) | 66.21 (18.18) |
| Mean inhalation volume, L (SD) | 1.16 (0.56) | 1.18 (0.52) | 1.30 (0.61) |
| Mean inhalation duration, seconds (SD) | 1.43 (0.62) | 1.45 (0.58) | 1.63 (0.88) |
| Mean albuterol inhalations, n/day (SD) | 3.54 (4.56) | 3.20 (4.03) | 2.61 (3.71) |

Baseline mean daily albuterol inhalations were higher and mean inhalation volume and duration were slightly lower for exacerbating patients compared with non-exacerbating patients. During the ±14-day AECOPD window, patients had higher daily albuterol inhalations than their baseline (outside the ±14-day AECOPD window) and compared with patients which did not have an AECOPD.

In contrast to the asthma exacerbation predictive model described above, it was found that the strongest predictive factor of COPD exacerbation was the parameter relating to air flow, e.g. peak inhalation flow, inhalation volume and/or inhalation duration. The number of rescue inhalations was also found to have significant predictive value.

On the basis of the above results, the weighted predictive model was developed to determine the probability of COPD exacerbation. The supervised machine learning technique, Gradient Boosting Trees, was used to solve the classification problem (yes/no COPD exacerbation in the upcoming x days (exacerbation period)). The Gradient Boosting Trees technique used was the same as that described above in relation to the asthma exacerbation prediction model.

Table 5 provides an exemplary list of factors which may be included in the weighted model, together with their relative weighting to each other.

TABLE 5

| Factor | | Label | Importance/Significance in the Model | Details |
|---|---|---|---|---|
| Biometric parameters | Demographics | Age | 1% | |
| | Vital signs | BMI | 1% | |
| | COPD history | Exacerbation history | 3% | Number of exacerbations in past 12 months; indication for hospitalization in past 12 months |
| Number of inhalations | | Features based on number of night inhalations | 11% | |
| | | Features based on number of inhalations | 6% | Baseline features, comparison to baseline and last 4 days features |
| Features based on inhalation parameters | | Features based on baseline inhalation parameters | 29% | |
| | | Comparison to baseline inhalation parameters | 20% | |
| | | Inhalation parameters during 4 days prior to prediction | 12% | |
| | | Inhalation parameters trends prior to prediction | 19% | |

The generated model was evaluated by receiver operating characteristic (ROC) curve analysis. Whilst the most significant factor in the predictive model for determining the probability of an impending COPD exacerbation is the inhalation parameter, the predictive model was strengthened by supplementing this with the data relating to the number of rescue inhalations. FIG. 17 shows a receiver operating characteristic (ROC) curve analysis of the model, which assesses the quality of the model by plotting the true positive rate against the false positive rate. This model predicted an impending exacerbation over the subsequent 5 days with an area under the ROC curve (AUC) value of 0.77.

In the case of COPD exacerbation prediction, the number of rescue inhalations may represent a significant factor in improving the accuracy with which the probability of an exacerbation may be determined, in spite of exerting less overall influence on the probability than the inhalation parameters.

FIGS. 18-22 provide a non-limiting example of an inhaler which may be included in the system 10.

FIG. 18 provides a front perspective view of a first inhaler 100, according to a non-limiting example. The inhaler 100 may, for example, be a breath-actuated inhaler. The inhaler 100 may include a top cap 102, a main housing 104, a mouthpiece 106, a mouthpiece cover 108, an electronics module 120, and/or an air vent 126. The mouthpiece cover 108 may be hinged to the main housing 104 so that it may open and close to expose the mouthpiece 106. Although illustrated as a hinged connection, the mouthpiece cover 106 may be connected to the inhaler 100 through other types of connections. Moreover, while the electronics module 120 is illustrated as housed within the top cap 102 at the top of the main housing 104, the electronics module 120 may be integrated and/or housed within main body 104 of the inhaler 100.

FIG. 19 provides a cross-sectional interior perspective view of the example inhaler 100. Inside the main housing 104, the inhaler 100 may include a medication reservoir 110 (e.g. a hopper), a bellows 112, a bellows spring 114, a yoke (not visible), a dosing cup 116, a dosing chamber 117, a deagglomerator 121, and a flow pathway 119. The medication reservoir 110 may include medication, such as dry powder medication, for delivery to the subject. When the mouthpiece cover 108 is moved from the closed to the open position, the bellows 112 may compress to deliver a dose of medication from the medication reservoir 110 to the dosing cup 116. Thereafter, a subject may inhale through the mouthpiece 106 in an effort to receive the dose of medication.

The airflow generated from the subject's inhalation may cause the deagglomerator 121 to aerosolize the dose of medication by breaking down the agglomerates of the medicament in the dose cup 116. The deagglomerator 121 may be configured to aerosolize the medication when the airflow through the flow pathway 119 meets or exceeds a particular rate, or is within a specific range. When aerosolized, the dose of medication may travel from the dosing cup 116, into the dosing chamber 117, through the flow pathway 119, and out of the mouthpiece 106 to the subject. If the airflow through the flow pathway 119 does not meet or exceed a particular rate, or is not within a specific range, the medication may remain in the dosing cup 116. In the event that the medication in the dosing cup 116 has not been aerosolized by the deagglomerator 121, another dose of medication may not be delivered from the medication reservoir 110 when the mouthpiece cover 108 is subsequently opened. Thus, a single dose of medication may remain in the dosing cup until the dose has been aerosolized by the deagglomerator 121. When a dose of medication is delivered, a dose confirmation may be stored in memory at the inhaler 100 as dose confirmation information.

As the subject inhales through the mouthpiece 106, air may enter the air vent to provide a flow of air for delivery of the medication to the subject. The flow pathway 119 may extend from the dosing chamber 117 to the end of the mouthpiece 106, and include the dosing chamber 117 and the internal portions of the mouthpiece 106. The dosing cup 116 may reside within or adjacent to the dosing chamber 117. Further, the inhaler 100 may include a dose counter 111 that is configured to be initially set to a number of total doses of medication within the medication reservoir 110 and to decrease by one each time the mouthpiece cover 108 is moved from the closed position to the open position.

The top cap 102 may be attached to the main housing 104. For example, the top cap 102 may be attached to the main housing 104 through the use of one or more clips that engage recesses on the main housing 104. The top cap 102 may overlap a portion of the main housing 104 when connected, for example, such that a substantially pneumatic seal exists between the top cap 102 and the main housing 104.

Figure 20:
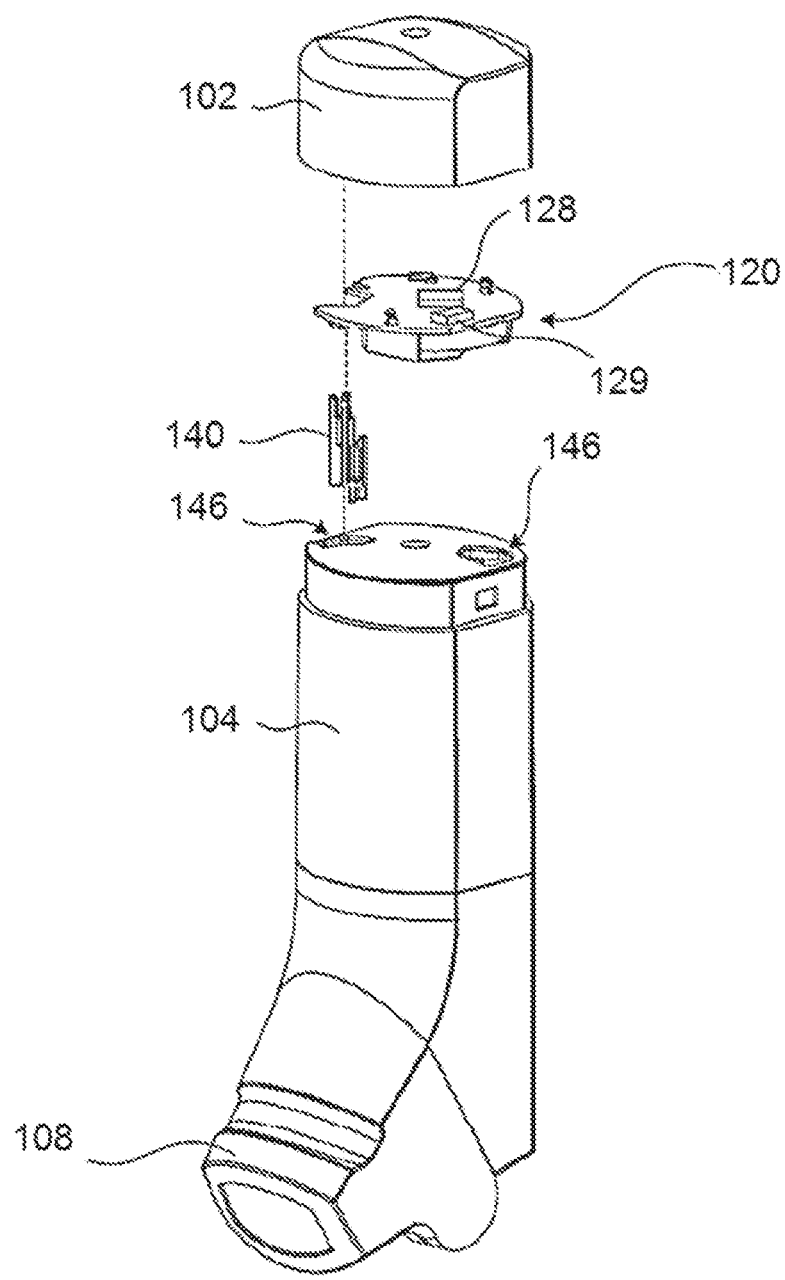
FIG. 20 provides an exploded perspective view of the example inhaler shown in FIG. 18.

FIG. 20 is an exploded perspective view of the example inhaler 100 with the top cap 102 removed to expose the electronics module 120. As shown in FIG. 20, the top surface of the main housing 104 may include one or more (e.g. two) orifices 146. One of the orifices 146 may be configured to accept a slider 140. For example, when the top cap 102 is attached to the main housing 104, the slider 140 may protrude through the top surface of the main housing 104 via one of the orifices 146.

Figure 21:
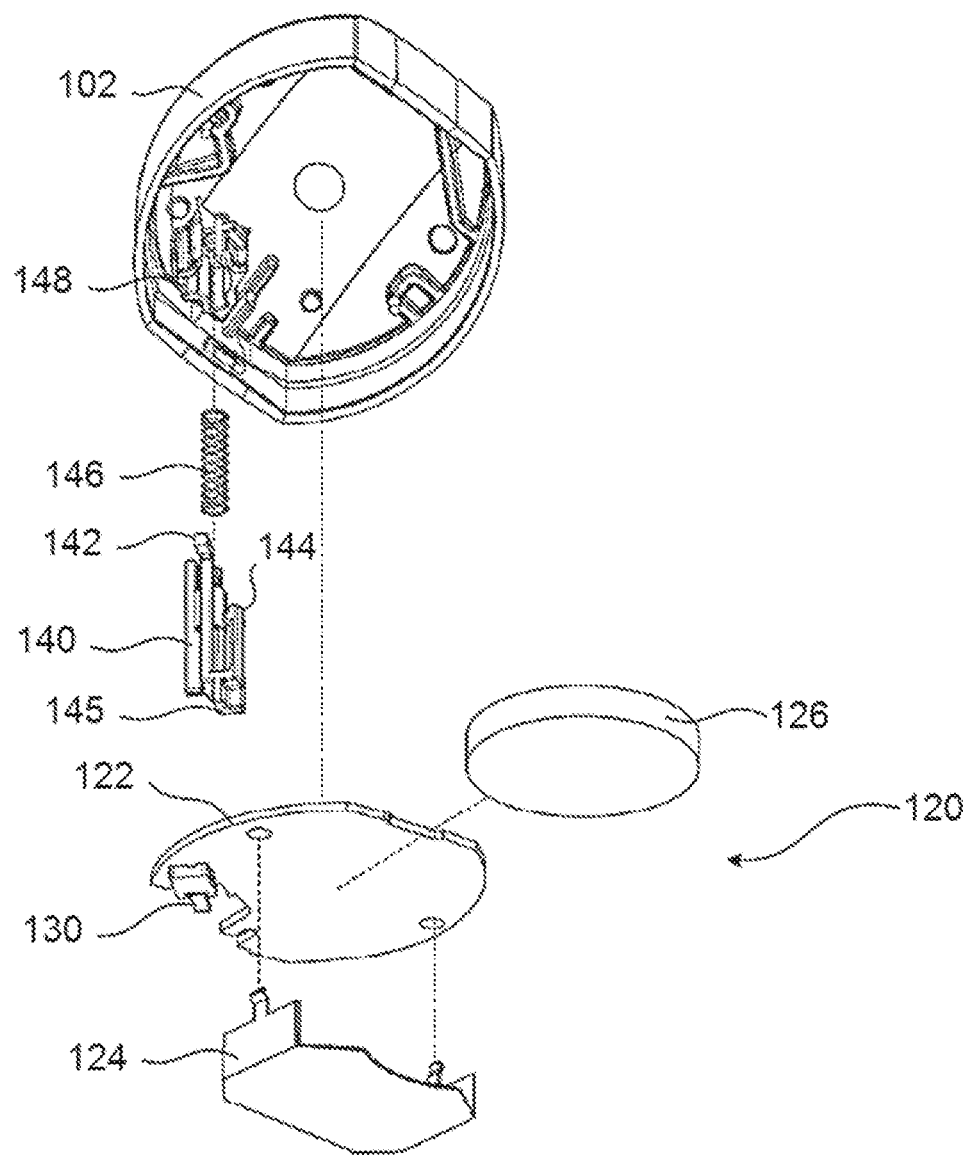
FIG. 21 provides an exploded perspective view of a top cap and electronics module of the inhaler shown in FIG. 18.

FIG. 21 is an exploded perspective view of the top cap 102 and the electronics module 120 of the example inhaler 100. As shown in FIG. 21, the slider 140 may define an arm 142, a stopper 144, and a distal end 145. The distal end 145 may be a bottom portion of the slider 140. The distal end 145 of the slider 140 may be configured to abut the yoke that resides within the main housing 104 (e.g. when the mouthpiece cover 108 is in the closed or partially open position). The distal end 145 may be configured to abut a top surface of the yoke when the yoke is in any radial orientation. For example, the top surface of the yoke may include a plurality of apertures (not shown), and the distal end 145 of the slider 140 may be configured to abut the top surface of the yoke, for example, whether or not one of the apertures is in alignment with the slider 140.

The top cap 102 may include a slider guide 148 that is configured to receive a slider spring 146 and the slider 140. The slider spring 146 may reside within the slider guide 148. The slider spring 146 may engage an inner surface of the top cap 102, and the slider spring 146 may engage (e.g. abut) an upper portion (e.g. a proximate end) of the slider 140. When the slider 140 is installed within the slider guide 148, the slider spring 146 may be partially compressed between the top of the slider 140 and the inner surface of the top cap 102. For example, the slider spring 146 may be configured such that the distal end 145 of the slider 140 remains in contact with the yoke when the mouthpiece cover 108 is closed.

The distal end 145 of the slider 145 may also remain in contact with the yoke while the mouthpiece cover 108 is being opened or closed. The stopper 144 of the slider 140 may engage a stopper of the slider guide 148, for example, such that the slider 140 is retained within the slider guide 148 through the opening and closing of the mouthpiece cover 108, and vice versa. The stopper 144 and the slider guide 148 may be configured to limit the vertical (e.g. axial) travel of the slider 140. This limit may be less than the vertical travel of the yoke. Thus, as the mouthpiece cover 108 is moved to a fully open position, the yoke may continue to move in a vertical direction towards the mouthpiece 106 but the stopper 144 may stop the vertical travel of the slider 140 such that the distal end 145 of the slider 140 may no longer be in contact with the yoke.

More generally, the yoke may be mechanically connected to the mouthpiece cover 108 and configured to move to compress the bellows spring 114 as the mouthpiece cover 108 is opened from the closed position and then release said compressed bellows spring 114 when the mouthpiece cover reaches the fully open position, thereby causing the bellows 112 to deliver the dose from the medication reservoir 110 to the dosing cup 116. The yoke may be in contact with the slider 140 when the mouthpiece cover 108 is in the closed position. The slider 140 may be arranged to be moved by the yoke as the mouthpiece cover 108 is opened from the closed position and separated from the yoke when the mouthpiece cover 108 reaches said fully open position. This arrangement may be regarded as a non-limiting example of the previously described dose metering assembly, since opening the mouthpiece cover 108 causes the metering of the dose of the medicament.

The movement of the slider 140 during the dose metering may cause the slider 140 to engage and actuate a switch 130. The switch 130 may trigger the electronics module 120 to register the dose metering. The slider 140 and switch 130 together with the electronics module 120 may thus correspond to a non-limiting example of the use-detection system 12B described above. The slider 140 may be regarded in this example as the means by which the use-detection system 12B is configured to register the metering of the dose by the dose metering assembly, each metering being thereby indicative of the inhalation performed by the subject using the inhaler 100.

Actuation of the switch 130 by the slider 140 may also, for example, cause the electronics module 120 to transition from the first power state to a second power state, and to sense an inhalation by the subject from the mouthpiece 106.

The electronics module 120 may include a printed circuit board (PCB) assembly 122, a switch 130, a power supply (e.g. a battery 126), and/or a battery holder 124. The PCB assembly 122 may include surface mounted components, such as a sensor system 128, a wireless communication circuit 129, the switch 130, and or one or more indicators (not shown), such as one or more light emitting diodes (LEDs). The electronics module 120 may include a controller (e.g. a processor) and/or memory. The controller and/or memory may be physically distinct components of the PCB 122. Alternatively, the controller and memory may be part of another chipset mounted on the PCB 122, for example, the wireless communication circuit 129 may include the controller and/or memory for the electronics module 120. The controller of the electronics module 120 may include a microcontroller, a programmable logic device (PLD), a microprocessor, an application specific integrated circuit (ASIC), a field programmable gate array (FPGA), or any suitable processing device or control circuit.

The controller may access information from, and store data in the memory. The memory may include any type of suitable memory, such as non-removable memory and/or removable memory. The non-removable memory may include random-access memory (RAM), read-only memory (ROM), a hard disk, or any other type of memory storage device. The removable memory may include a subscriber identity module (SIM) card, a memory stick, a secure digital (SD) memory card, and the like. The memory may be internal to the controller. The controller may also access data from, and store data in, memory that is not physically located within the electronics module 120, such as on a server or a smart phone.

Figure 19:
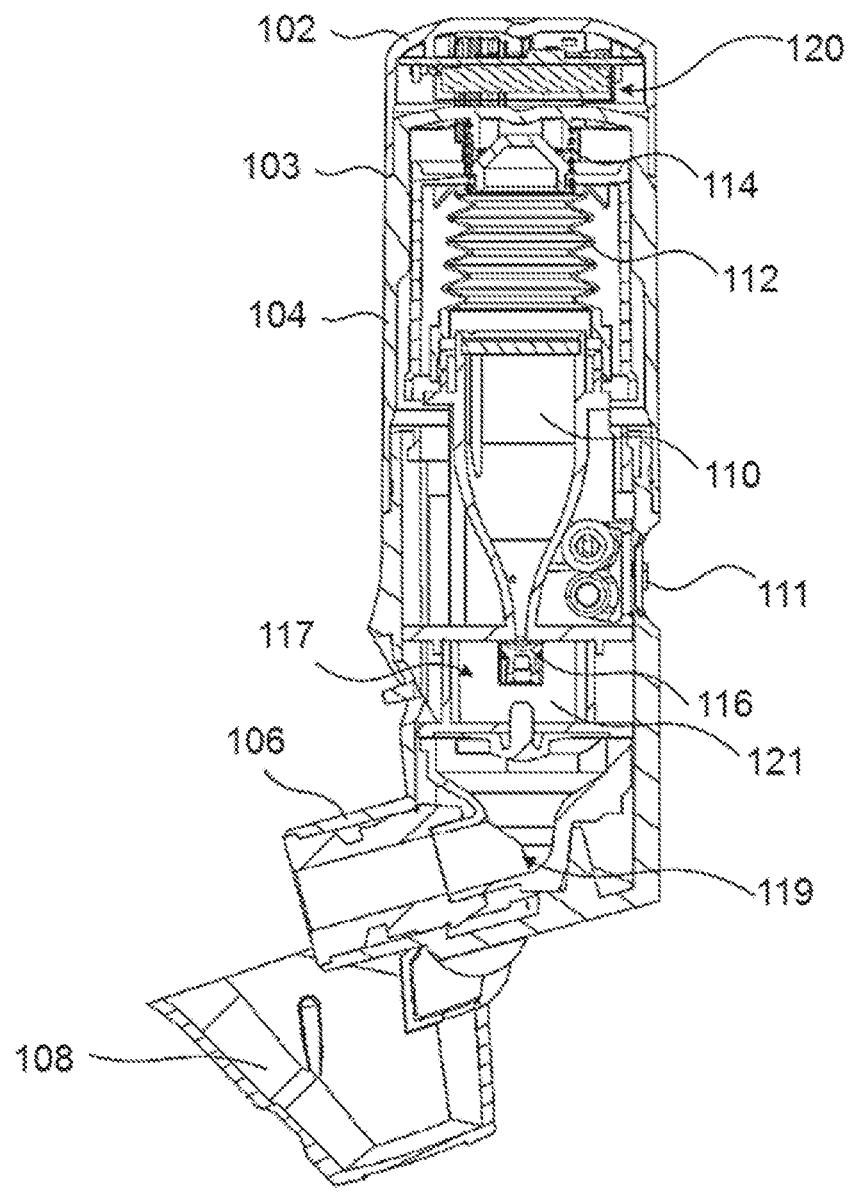
FIG. 19 shows a cross-sectional interior perspective view of the inhaler shown in FIG. 18.

The sensor system 128 may include one or more sensors. The sensor system 128 may be an example of the sensor system 12A. The sensor system 128 may include one or more sensors, for example, of different types, such as, but not limited to one or more pressure sensors, temperature sensors, humidity sensors, orientation sensors, acoustic sensors, and/or optical sensors. The one or more pressure sensors may include a barometric pressure sensor (e.g. an atmospheric pressure sensor), a differential pressure sensor, an absolute pressure sensor, and/or the like. The sensors may employ microelectromechanical systems (MEMS) and/or nanoelectromechanical systems (NEMS) technology. The sensor system 128 may be configured to provide an instantaneous reading (e.g. pressure reading) to the controller of the electronics module 120 and/or aggregated readings (e.g. pressure readings) over time. As illustrated in FIGS. 19 and 20, the sensor system 128 may reside outside the flow pathway 119 of the inhaler 100, but may be pneumatically coupled to the flow pathway 119.

The controller of the electronics module 120 may receive signals corresponding to measurements from the sensor system 128. The controller may calculate or determine one or more airflow metrics using the signals received from the sensor system 128. The airflow metrics may be indicative of a profile of airflow through the flow pathway 119 of the inhaler 100. For example, if the sensor system 128 records a change in pressure of 0.3 kilopascals (kPa), the electronics module 120 may determine that the change corresponds to an airflow rate of approximately 45 liters per minute (Lpm) through the flow pathway 119.

Figure 22:
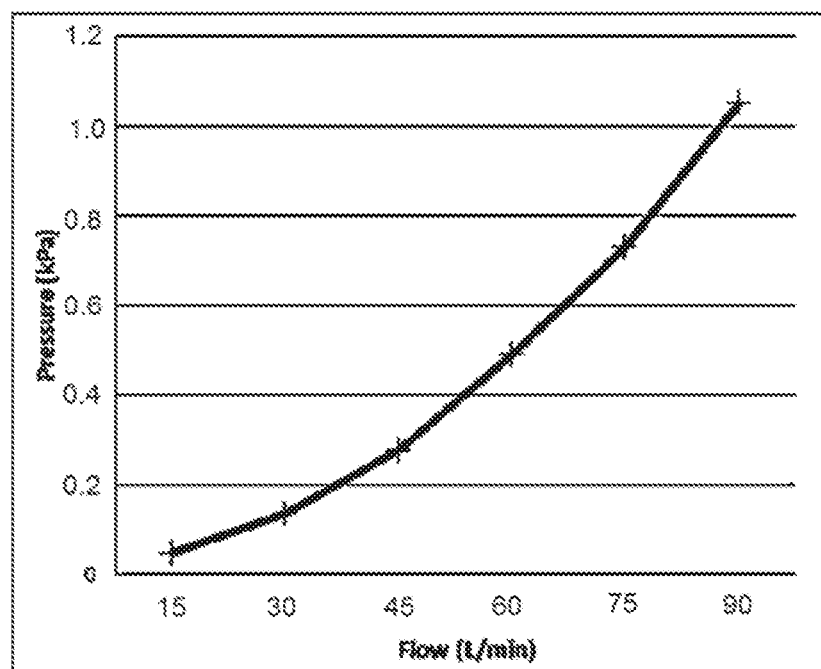
FIG. 22 shows a graph of airflow rate through the example inhaler shown in FIG. 18 versus pressure.

FIG. 22 shows a graph of airflow rates versus pressure. The airflow rates and profile shown in FIG. 22 are merely examples and the determined rates may depend on the size, shape, and design of the inhalation deice 100 and its components.

The controller of the electronics module 120 may generate personalized data in real-time by comparing signals received from the sensor system 128 and/or the determined airflow metrics to one or more thresholds or ranges, for example, as part of an assessment of how the inhaler 100 is being used and/or whether the use is likely to result in the delivery of a full dose of medication. For example, where the determined airflow metric corresponds to an inhalation with an airflow rate below a particular threshold, the electronics module 120 may determine that there has been no inhalation or an insufficient inhalation from the mouthpiece 106 of the inhaler 100. If the determined airflow metric corresponds to an inhalation with an airflow rate above a particular threshold, the electronics module 120 may determine that there has been an excessive inhalation from the mouthpiece 106. If the determined airflow metric corresponds to an inhalation with an airflow rate within a particular range, the electronics module 120 may determine that the inhalation is "good", or likely to result in a full dose of medication being delivered.

The pressure measurement readings and/or the computed airflow metrics may be indicative of the quality or strength of inhalation from the inhaler 100. For example, when compared to a particular threshold or range of values, the readings and/or metrics may be used to categorize the inhalation as a certain type of event, such as a good inhalation event, a low inhalation event, a no inhalation event, or an excessive inhalation event. The categorization of the inhalation may be usage parameters stored as personalized data of the subject.

The no inhalation event may be associated with pressure measurement readings and/or airflow metrics below a particular threshold, such as an airflow rate less than 30 Lpm. The no inhalation event may occur when a subject does not inhale from the mouthpiece 106 after opening the mouthpiece cover 108 and during the measurement cycle. The no inhalation event may also occur when the subject's inspiratory effort is insufficient to ensure proper delivery of the medication via the flow pathway 119, such as when the inspiratory effort generates insufficient airflow to activate the deagglomerator 121 and, thus, aerosolize the medication in the dosing cup 116.

The low inhalation event may be associated with pressure measurement readings and/or airflow metrics within a particular range, such as an airflow rate between 30 Lpm and 45 Lpm. The low inhalation event may occur when the subject inhales from the mouthpiece 106 after opening the mouthpiece cover 108 and the subject's inspiratory effort causes at least a partial dose of the medication to be delivered via the flow pathway 119. That is, the inhalation may be sufficient to activate the deagglomerator 121 such that at least a portion of the medication is aerosolized from the dosing cup 116.

The good inhalation event may be associated with pressure measurement readings and/or airflow metrics above the low inhalation event, such as an airflow rate between 45 Lpm and 200 Lpm. The good inhalation event may occur when the subject inhales from the mouthpiece 106 after opening the mouthpiece cover 108 and the subject's inspiratory effort is sufficient to ensure proper delivery of the medication via the flow pathway 119, such as when the inspiratory effort generates sufficient airflow to activate the deagglomerator 121 and aerosolize a full dose of medication in the dosing cup 116.

The excessive inhalation event may be associated with pressure measurement readings and/or airflow metrics above the good inhalation event, such as an airflow rate above 200 Lpm. The excessive inhalation event may occur when the subject's inspiratory effort exceeds the normal operational parameters of the inhaler 100. The excessive inhalation event may also occur if the device 100 is not properly positioned or held during use, even if the subject's inspiratory effort is within a normal range. For example, the computed airflow rate may exceed 200 Lpm if the air vent is blocked or obstructed (e.g. by a finger or thumb) while the subject is inhaling from the mouthpiece 106.

Any suitable thresholds or ranges may be used to categorize a particular event. Some or all of the events may be used. For example, the no inhalation event may be associated with an airflow rate below 45 Lpm and the good inhalation event may be associated with an airflow rate between 45 Lpm and 200 Lpm. As such, the low inhalation event may not be used at all in some cases.

The pressure measurement readings and/or the computed airflow metrics may also be indicative of the direction of flow through the flow pathway 119 of the inhaler 100. For example, if the pressure measurement readings reflect a negative change in pressure, the readings may be indicative of air flowing out of the mouthpiece 106 via the flow pathway 119. If the pressure measurement readings reflect a positive change in pressure, the readings may be indicative of air flowing into the mouthpiece 106 via the flow pathway 119. Accordingly, the pressure measurement readings and/or airflow metrics may be used to determine whether a subject is exhaling into the mouthpiece 106, which may signal that the subject is not using the device 100 properly.

The inhaler 100 may include a spirometer or similarly operating device to enable measurement of lung function metrics. For example, the inhaler 100 may perform measurements to obtain metrics related to a subject's lung capacity. The spirometer or similarly operating device may measure the volume of air inhaled and/or exhaled by the subject. The spirometer or similarly operating device may use pressure transducers, ultrasound, or a water gauge to detect the changes in the volume of air inhaled and/or exhaled.

The personalized data collected from, or calculated based on, the usage of the inhaler 100 (e.g. pressure metrics, airflow metrics, lung function metrics, dose confirmation information, etc.) may be computed and/or assessed via external devices as well (e.g. partially or entirely). More specifically, the wireless communication circuit 129 in the electronics module 120 may include a transmitter and/or receiver (e.g. a transceiver), as well as additional circuitry. For example, the wireless communication circuit 129 may include a Bluetooth chip set (e.g. a Bluetooth Low Energy chip set), a ZigBee chipset, a Thread chipset, etc. As such, the electronics module 120 may wirelessly provide the personalized data, such as pressure measurements, airflow metrics, lung function metrics, dose confirmation information, and/or other conditions related to usage of the inhaler 100, to an external device, including a smart phone. The personalized data may be provided in real time to the external device to enable exacerbation risk prediction based on real-time data from the inhaler 100 that indicates time of use, how the inhaler 100 is being used, and personalized data about the user of the inhaler, such as real-time data related to the subject's lung function and/or medical treatment. The external device may include software for processing the received information and for providing compliance and adherence feedback to users of the inhaler 100 via a graphical user interface (GUI).

The airflow metrics may include personalized data that is collected from the inhaler 100 in real-time, such as one or more of an average flow of an inhalation/exhalation, a peak flow of an inhalation/exhalation (e.g. a maximum inhalation received), a volume of an inhalation/exhalation, a time to peak of an inhalation/exhalation, and/or the duration of an inhalation/exhalation. The airflow metrics may also be indicative of the direction of flow through the flow pathway 119. That is, a negative change in pressure may correspond to an inhalation from the mouthpiece 106, while a positive change in pressure may correspond to an exhalation into the mouthpiece 106. When calculating the airflow metrics, the electronics module 120 may be configured to eliminate or minimize any distortions caused by environmental conditions. For example, the electronics module 120 may re-zero to account for changes in atmospheric pressure before or after calculating the airflow metrics. The one or more pressure measurements and/or airflow metrics may be time-stamped and stored in the memory of the electronics module 120.

In addition to the airflow metrics, the inhaler 100, or another computing device, may use the airflow metrics to generate additional personalized data. For example, the controller of the electronics module 120 of the inhaler 100 may translate the airflow metrics into other metrics that indicate the subject's lung function and/or lung health that are understood to medical practitioners, such as peak inspiratory flow metrics, peak expiratory flow metrics, and/or forced expiratory volume in 1 second (FEV1), for example. The electronics module 120 of the inhaler may determine a measure of the subject's lung function and/or lung health using a mathematical model such as a regression model. The mathematical model may identify a correlation between the total volume of an inhalation and FEV1. The mathematical model may identify a correlation between peak inspiratory flow and FEV1. The mathematical model may identify a correlation between the total volume of an inhalation and peak expiratory flow. The mathematical model may identify a correlation between peak inspiratory flow and peak expiratory flow.

The battery 126 may provide power to the components of the PCB 122. The battery 126 may be any suitable source for powering the electronics module 120, such as a coin cell battery, for example. The battery 126 may be rechargeable or non-rechargeable. The battery 126 may be housed by the battery holder 124. The battery holder 124 may be secured to the PCB 122 such that the battery 126 maintains continuous contact with the PCB 122 and/or is in electrical connection with the components of the PCB 122. The battery 126 may have a particular battery capacity that may affect the life of the battery 126. As will be further discussed below, the distribution of power from the battery 126 to the one or more components of the PCB 122 may be managed to ensure the battery 126 can power the electronics module 120 over the useful life of the inhaler 100 and/or the medication contained therein.

In a connected state, the communication circuit and memory may be powered on and the electronics module 120 may be "paired" with an external device, such as a smart phone. The controller may retrieve data from the memory and wirelessly transmit the data to the external device. The controller may retrieve and transmit the data currently stored in the memory. The controller may also retrieve and transmit a portion of the data currently stored in the memory. For example, the controller may be able to determine which portions have already been transmitted to the external device and then transmit the portion(s) that have not been previously transmitted. Alternatively, the external device may request specific data from the controller, such as any data that has been collected by the electronics module 120 after a particular time or after the last transmission to the external device. The controller may retrieve the specific data, if any, from the memory and transmit the specific data to the external device.

The data stored in the memory of the electronics module 120 (e.g. the signals generated by the switch 130, the pressure measurement readings taken by the sensory system 128 and/or the airflow metrics computed by the controller of the PCB 122) may be transmitted to an external device, which may process and analyze the data to determine the usage parameters associated with the inhaler 100. Further, a mobile application residing on the mobile device may generate feedback for the user based on data received from the electronics module 120. For example, the mobile application may generate daily, weekly, or monthly report, provide confirmation of error events or notifications, provide instructive feedback to the subject, and/or the like.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

What is claimed is:

1. A method for determining a probability of an asthma exacerbation, the method comprising:
   determining a number of inhalations performed by a user on an inhaler using at least one sensor of the inhaler, wherein each inhalation is associated with delivery of medication to the user;
   determining an airflow parameter for each of the inhalations using the at least one sensor;
   determining a probability of the asthma exacerbation for the user using a trained machine learning model based on a number of inhalations performed by the user on the inhaler over a predetermined previous number of days, an airflow parameter for each of the inhalations performed by the user during use of the inhaler over the predetermined previous number of days, and a comparison of a baseline value for the airflow parameter to the airflow parameter for each of the inhalations performed by the user during use of the inhaler over the predetermined previous number of days; and
   generating a notification, via a display device, indicating the probability of the asthma exacerbation for the user.

2. The method of claim 1, wherein the airflow parameter comprises at least one of a peak inhalation flow, an inhalation volume, or an inhalation duration.

3. The method of claim 1, wherein the predetermined previous number of days is the previous four days.

4. The method of claim 1, wherein the number of inhalations performed by the user on the inhaler over the predetermined previous number of days comprises a mean number of inhalations per day over the predetermined number of days.

5. The method of claim 1, further comprising:
   determining the probability of the asthma exacerbation for the user using the trained machine learning model further based on a number of night-time inhalations performed by the user during use of the inhaler.

6. The method of claim 1, wherein each of the inhalations are associated with delivery of a rescue medication to the user.

7. The method of claim 1, further comprising:
   determining that the probability of the asthma exacerbation is greater than a predetermined upper threshold; and
   updating a treatment regimen associated with the user in response to the determination that the probability of the asthma exacerbation is greater than the predetermined upper threshold, wherein the updated treatment regimen comprises the administration of a biologics medication to the subject.

8. The method of claim 7 wherein the updated treatment regimen comprises the administration of one or more of mepolizumab, reslizumab, benralizumab, or dupilumab.

9. The method of claim 1, wherein an exacerbation comprises moderate or severe clinical asthma exacerbations (CAE), wherein a severe CAE is characterized as an event that requires oral steroid for at least three days and hospitalization, and a moderate CAE is characterized as an event that requires oral steroid for at least three days or hospitalization.

10. The method of claim 1, wherein the probability of the asthma exacerbation is associated within an exacerbation period of time that is within the next one to ten days.

11. The method of claim 1, wherein the at least one sensor comprises one or more pressure sensors, temperature sensors, humidity sensors, orientation sensors, acoustic sensors, and/or optical sensors.

12. The method of claim 1, wherein the airflow parameter comprises peak inhalation flow; and
   wherein the method further comprises:
   determining a change in peak inhalation flow for the user; and
   determining the probability of the asthma exacerbation for the user using the trained machine learning model further based on the change in peak inhalation flow for the user.

13. The method of claim 1, wherein the at least one sensor comprises a first sensor and a second sensor, wherein the first sensor determines the number of inhalations and the second sensor determines the airflow parameter.

14. The method of claim 1, wherein the airflow parameter comprises inhalation volume; and
   wherein the method further comprises:
   determining a change in inhalation volume for the user; and
   determining the probability of the asthma exacerbation for the user using the trained machine learning model further based on the change in inhalation volume for the user.

15. A computer-readable medium having stored thereon instructions that, when executed by a processor, cause the processor to:
   determine a plurality of inhalations performed by a plurality of users on a plurality of inhalers, wherein each inhaler comprises at least one sensor, wherein each inhalation is associated with delivery of medication to the user;
   determine an airflow parameter for each of the plurality of inhalations using the at least one sensor of the respective inhaler; and
   train a machine learning model to determine a probability of the asthma exacerbation for a user based on the plurality of inhalations performed by the plurality of users, an airflow parameter for each of the plurality of inhalations, and a comparison of a baseline value for the airflow parameter for each respective user to the airflow parameter for each of the plurality of inhalations performed by each respective user.

16. The computer-readable medium of claim 15, wherein the airflow parameter comprises at least one of a peak inhalation flow, an inhalation volume, or an inhalation duration.

17. The computer-readable medium of claim 15, wherein the computer-readable medium has stored thereon instructions that, when executed by the processor, cause the processor to:
   train the machine learning model further based on whether each of the plurality of inhalations are night-time inhalations of a rescue medicament.

18. The computer-readable medium of claim 15, wherein the computer-readable medium has stored thereon instructions that, when executed by the processor, cause the processor to:
   determine that the probability of the asthma exacerbation for the user is greater than a predetermined upper threshold; and
   update a treatment regimen associated with the user in response to the determination that the probability of the asthma exacerbation is greater than the predetermined upper threshold, wherein the updated treatment regimen comprises the administration of a biologics medication to the subject, wherein the updated treatment regimen comprises the administration of one or more of mepolizumab, reslizumab, benralizumab, or dupilumab.

19. A system for determining a probability of an asthma exacerbation, the system comprising:
an inhaler configured to deliver a medicament to a user, the inhaler comprising a processor, a memory, a transceiver, and a sensor, wherein the processor of the inhaler is configured to:
detect, via the sensor, inhalations performed by the user during a use of the inhaler;
measure airflow parameters for each of the inhalations, wherein the airflow parameter for each of the inhalations comprise at least one of a peak inhalation flow, an inhalation volume, or an inhalation duration; and
transmit, via the transceiver, indications of the airflow parameters for each of the inhalations; and
a computer-readable medium having stored thereon instructions that, when executed by a processor, cause the processor to:
determine a number of inhalations performed by the user during a use of the inhaler;
determine the airflow parameters for each of the inhalations;
determine a probability of the asthma exacerbation for the user using a trained machine learning model based on a number of inhalations performed by the user on the inhaler over a predetermined previous number of days, an airflow parameter for each of the inhalations performed by the user during use of the inhaler over the predetermined previous number of days, and a comparison of a baseline value for the airflow parameter to the airflow parameter for each of the inhalations performed by the user during use of the inhaler over the predetermined previous number of days; and
generate a notification, via a display device, indicating the probability of the asthma exacerbation for the user.

20. The system of claim 19, wherein the inhaler comprises:
an electronics module comprising the processor, the memory, the transceiver, and the sensor;
a medication reservoir comprising medicament;
a mouthpiece cover; and
a yoke mechanically connected to the mouthpiece cover, wherein the yoke is configured to move to as the mouthpiece cover is opened from a closed position to an open position to cause a dose of medicament to be delivered from the medication reservoir and cause the electronics module to change power states.

* * * * *